United States Patent [19]

Hafeman

[11] Patent Number: 4,963,815
[45] Date of Patent: Oct. 16, 1990

[54] PHOTORESPONSIVE ELECTRODE FOR DETERMINATION OF REDOX POTENTIAL

[75] Inventor: Dean Hafeman, Hillsborough, Calif.

[73] Assignee: Molecular Devices Corporation, Palo Alto, Calif.

[21] Appl. No.: 72,168

[22] Filed: Feb. 10, 1987

[51] Int. Cl.$^5$ ............... G01N 27/07; G01N 27/56; G01N 21/27

[52] U.S. Cl. .................... 324/715; 204/403; 204/153.1; 204/153.21; 324/438; 435/4

[58] Field of Search ............ 324/71.5, 71.1, 438, 324/439, 425; 204/1 T, 403, 412; 435/7, 29, 34, 817, 4, 39

[56] References Cited

U.S. PATENT DOCUMENTS

| | | | |
|---|---|---|---|
| 3,825,483 | 7/1974 | Nakamura | 324/438 X |
| 4,020,830 | 5/1977 | Johnson et al. | 324/425 X |
| 4,562,157 | 12/1985 | Lowe et al. | 324/71.5 X |
| 4,591,550 | 5/1986 | Hafeman et al. | 324/71.5 X |
| 4,704,353 | 11/1987 | Humphries et al. | 324/71.5 X |

Primary Examiner—Reinhard J. Eisenzopf
Assistant Examiner—Robert W. Mueller
Attorney, Agent, or Firm—Allegretti & Witcoff

[57] ABSTRACT

Devices and methods are provided for determining the presence and amount of an analyte by measuring a redox potential-modulated photoinducing signal from a photoresponsive element. Further devices and methods are provided for determining the presence and amount of an analyte by measuring a redox potential, pH or ion modulated photoinduced signal from a photoresponsive element, where one signal is a constant system and the other signal(s) is a variable system. The constant system signal is used to standardize the variable system signal. Various protocols may be employed where an analyte may be directly or indirectly coupled to a redox couple, a pH or ion system for detection. The latter devices employ a photoresponsive element having a medium contacting surface, which is partially covered with an electronically conducting layer and partially covered with a protective insulative layer.

38 Claims, 9 Drawing Sheets

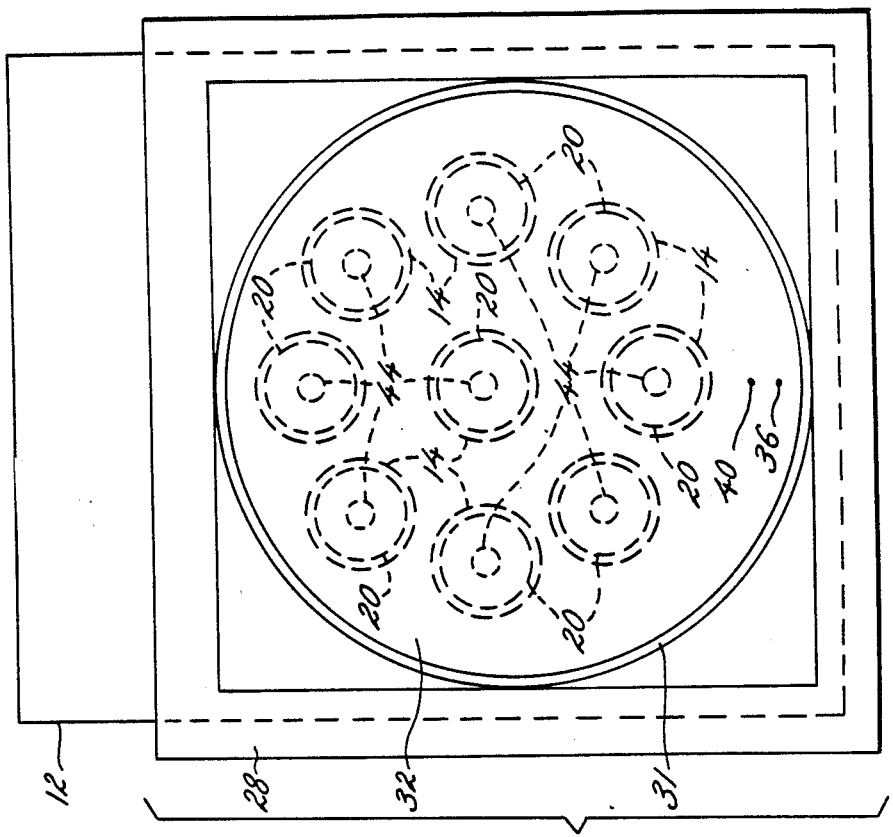
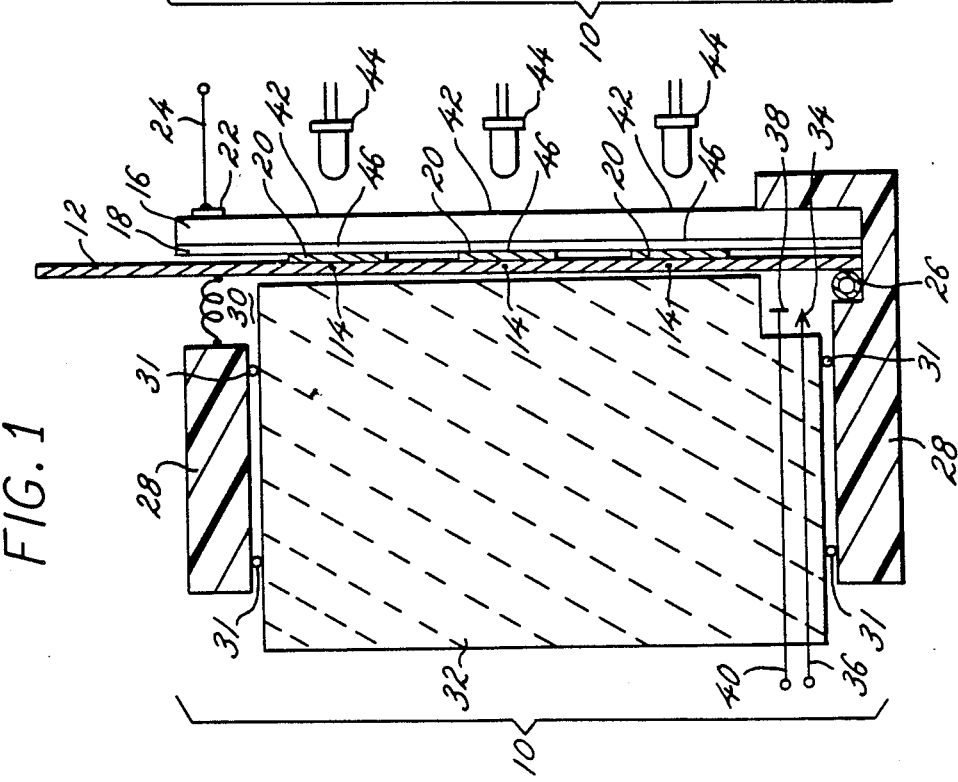

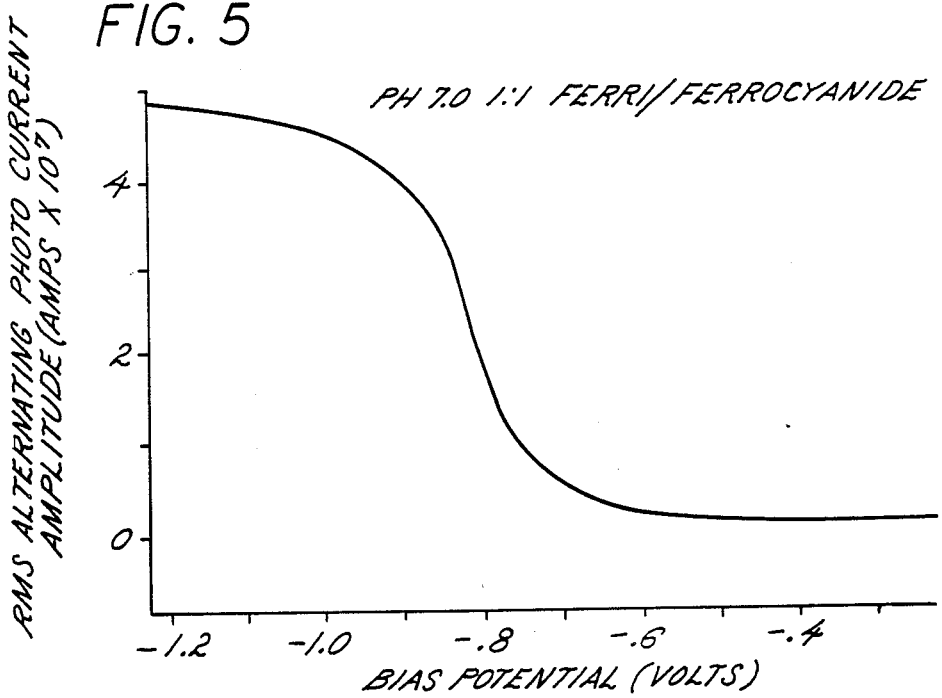
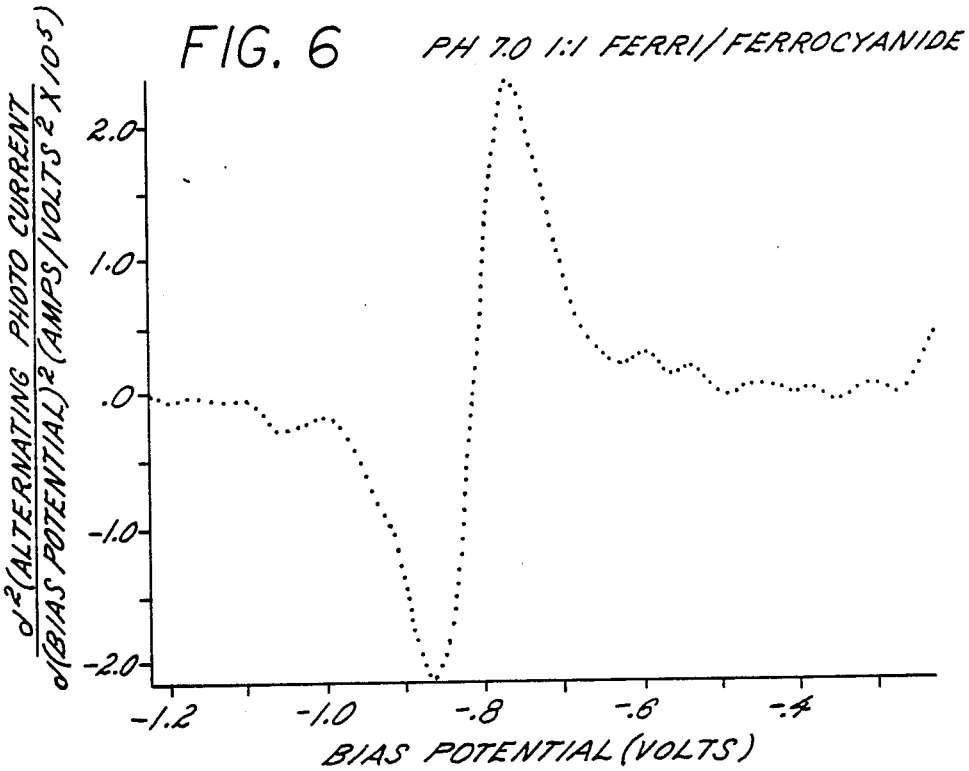

pH 1.00, pH 7.00, pH 10.00 ON SILICON NITRIDE INSULATOR pH RESPONSE TO LIGHT ADDRESSED SILICON NITRIDE GATE

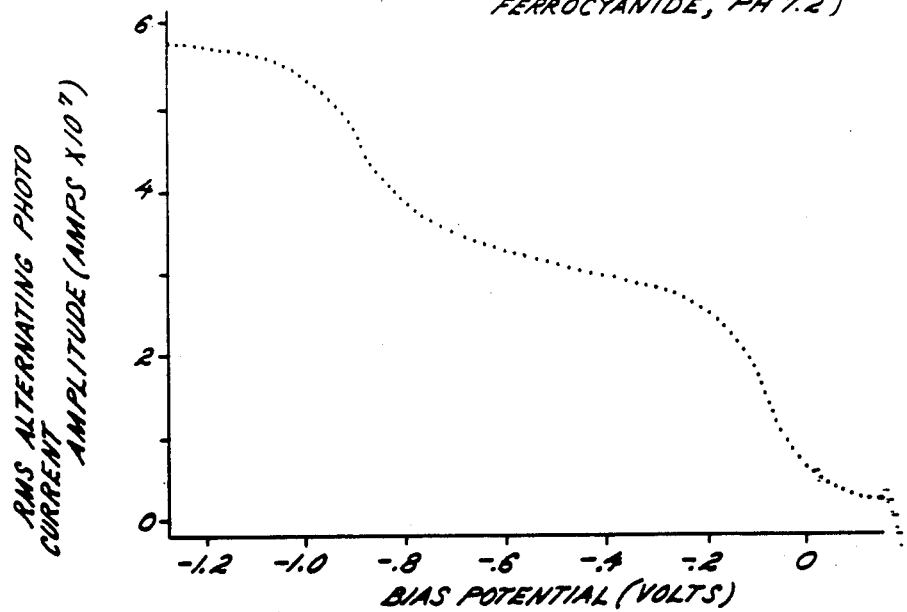
FIG. 11 PARTIAL GOLD ON SILICON NITRIDE (1:1 FERRI/FERROCYANIDE, PH 7.2)
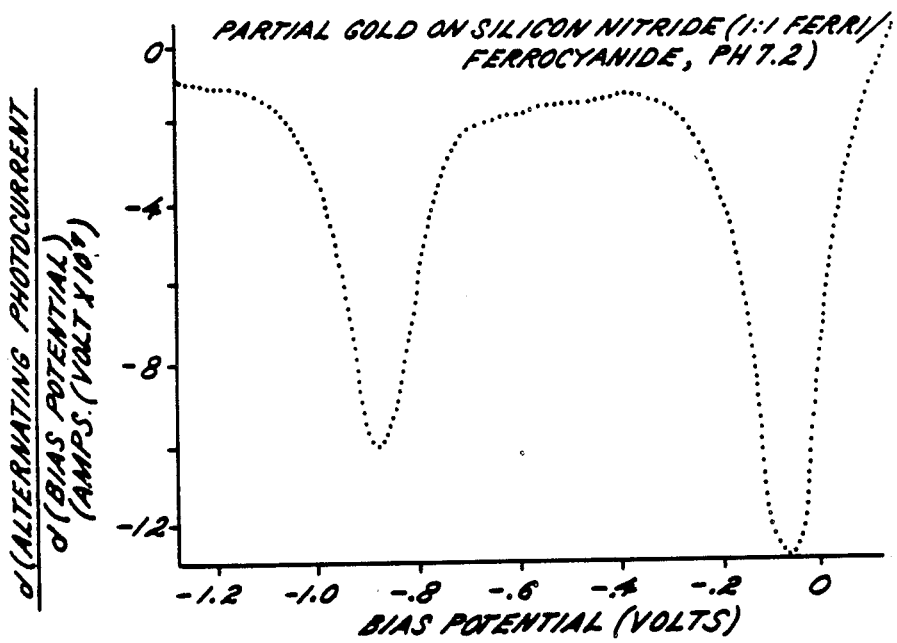
FIG. 12 PARTIAL GOLD ON SILICON NITRIDE (1:1 FERRI/FERROCYANIDE, PH 7.2)

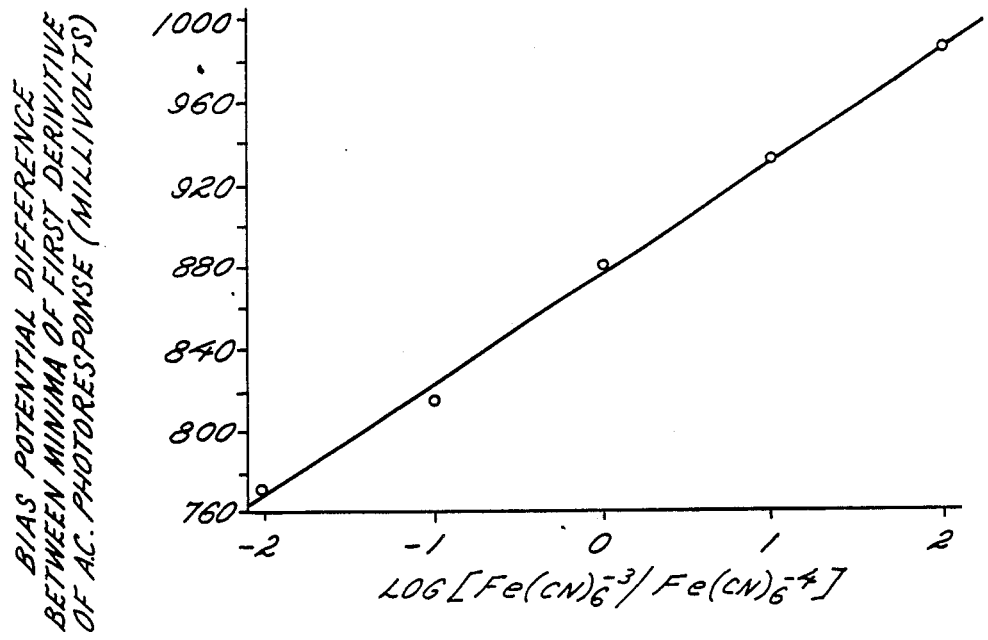
FIG. 14 — RESPONSE OF REDOX SENSOR WITHOUT REFERENCE ELECTRODE
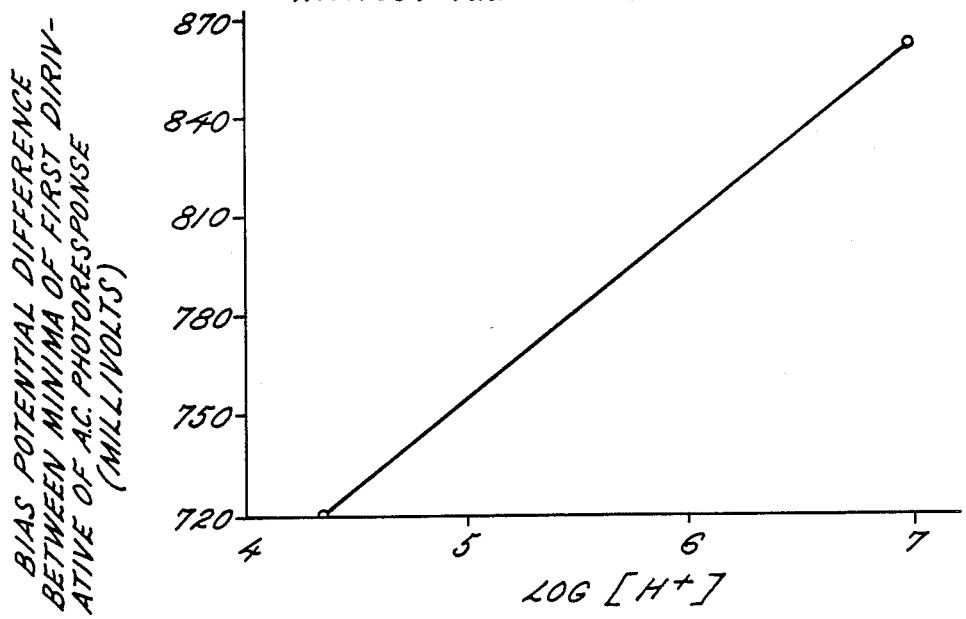
FIG. 15 — RESPONSE OF PH SENSOR WITHOUT REFERENCE ELECTRODE

4,963,815

PHOTORESPONSIVE ELECTRODE FOR DETERMINATION OF REDOX POTENTIAL

INTRODUCTION

1. Technical Field

The invention concerns electronic devices for measuring redox potential in an electrolyte and for measuring the rate of change in redox potential in electrodes containing an analyte where the analyte is made to effect a change in redox potential.

2. Background

Industry, medicine, and other areas are frequently involved with the measurement of a continuously extending list of analytes. There exists today a large number of different devices and protocols for determining analytes in process streams, physiological fluids, and environmental substances. Each of these devices has a variety of advantages and disadvantages. In any device, one is concerned with the economics of its production, it sensitivity, reliability, lifetime, ease of use, and adaptability to different media and analytes.

One of the problems associated with sensitive measurement of redox species or redox reactions with a redox electrode is that stray currents within the electrochemical measurement cell or within the circuitry attached to the redox electrode introduce error into the measurement. Such stray-currents may arise from a number of sources including corrosion reactions within the cell, electrical short circuits, or pickup of electrical noise from the environment. It is therefore desirable to minimize these sources of measurement error by using corrosion resistant materials and by employing measurement devices and circuitry configurations which reliably minimize stray currents. Additionally, in aqueous environments, another problem associated with sensitive measurement of redox species is the need for a stable, liquid junciton, reference electrode. Such reference electrodes are costly and icovenient to provide in otherwise solid-state measurement devices. Also, reference electrodes can be unreliable in commercial use, because various reference electrodes, such as liquid reference electrodes tend to show drift in potential. In this situation, one must find some way to compensate for the change in potential of the reference electrode in order to be able to compare results obtained at different times. There is therefore, an interest in finding techniques to obviate the need for a liquid reference electrode or provide an alternative standard of reference.

DESCRIPTION OF THE RELEVANT LITERATURE

U.S. Pat. No. 4,490,216 describes a lipid membrane containing electronanalytical element. U.S. Pat. No. 4,591,550 describes the use of monolithic semiconductors for determining a plurality of samples at different sites on the semiconductor, interrogating various sites of the semiconductor with light. U.S. Pat. Nos. 4,020,820, 4,322,680, and 4,397,714 describe the use of chemically-sensitive field effect transistors to detect redox compounds.

SUMMARY OF THE INVENTION

Methods and photoresponsive field effect devices are provided for detecting a wide variety of analytes, employing a photoresponsive substrate in connection with a metal electrode. Preferably, the metal electrode is in the form of a metal layer positioned on the surface of an insulative layer, which in turn is positioned on the photoresponsive substrate. The sample medium includes a redox couple, where the potential of the redox couple may be related to the standard potential of the redox coupled and the ratio of reduced and oxidized members of the redox pair. The presence and amount of an analyte may be detected by its effect on the ratio of reduced and oxidized members fo the redox pair and thus upon the redox potential.

Measurements are made on the medium by photoresponsively monitoring electrical-field-effects within a surface region of the photoresponsive substrate, where the potential on the isolated metal electrode affects the electrical field within such region. Various measurement may be employed to monitor photoresponsively electrical-field-effects within such region of the photoresponsive substrate, including montoring photoconductance, photocapacitance, photovoltage, or photocurrent.

The need for a liquid junction reference electrode is obviated by monitoring photoresponsively both (a) the redox potential at a first surface region of the photoresponsive substrate, where the electrical field is influenced by the redox potential of the medium in contact with the metal layer; and (b) monitoring the electrical field at a second surface region of the phtoresponsive substrate, where the electrical field is substantially independent of the redox potential of the medium or varies in a know manner different from the variation at the first site. The response as measured at the first and second sites may be compared so as to determine the relative difference in redox potential of electrolytes of different composition present at the first and second sites or to determine the change in redox potential over time at one site with respect to the electrical field at the other site.

BRIEF DESCRIPTION OF THE DRAWINGS

FIG. 1 is a diagrammatic cross-sectional view of a device accordng to this invention;

FIG. 2 is a plan view of a multiunit device according to FIG. 1;

FIGS. 5 and 6 are graphs of the results obtained with a ferri/ferrocyanide couple with the bias potential an ordinate and the alternating photocurrent as abscissa, with FIG. 6 as the second derivative of the graph of FIG. 5;

FIG. 11 is a graph of the alternating photocurrent amplitude as a function of bias potential resulting from illumination of both redox potential and pH sensitive regions of a photoresponsive electrode;

FIG. 12 is a graph of the first derivative of the result of FIG. 11;

FIG. 14 is a graph of the difference in bias potential between the two minima in the first derivative of the alternating photocurrent amplitude vs. bias potential response where the circuit and device as shown in FIG. 13 were employed while the pH is kept constant at 7.0 and the redox potential was varied;

FIG. 15 is a graph of the difference in bias potential between the two minima in the first derivative of the alternating photocurrent amplitude vs. bias potential response where the circuit and device as shown in FIG. 13 were employed while the pH is varied and the redox potential is held constant.

DESCRIPTION OF THE SPECIFIC EMBODIMENTS

Figure 3:
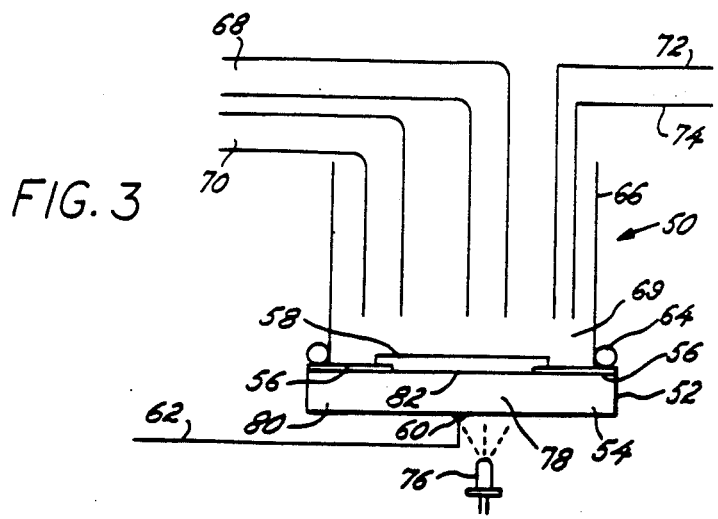
FIG. 3 is a diagrammatic view of a single unit device.

Electrochemical methods and photoresponsive devices are provided for determining the state of an electrolyte medium where the state affects the measured redox potential of the medium. The redox potential of the electrolyte medium is monitored with an electrochemical measurement cell employing two or more electrodes. The first electode is a working electrode comprised of a photoresponsive substrate with an electronically conductive layer in contact with the electrolyte. In the preferred mode, an electrically insulating layer is placed between the photoresponsive substrate and the surface of the electronically conductive layer. The insulating layer is sufficently thin, so that the potential of the electronically conductive layer substantially affects the electrical field within a surface region of the photoresponsive substrate. Also, in one embodiment, a portion of the insulating layer is free of the electronically conductive layer, so as to be be in direct contact with the electrolyte to provide a redox potential independent photoresponse. The second electrode may be a potential-stable, liquid junction reference electrode or a less potential-stable controlling electrode. Alternatively, both the reference electrode and the controlling electrode may be employed together with the working photoresponsive electrode to form a 3-electrode electrochemical cell.

The redox potential of the electrolyte determines the potential of the electronically conductive layer on the working electrode. The potential of the electronically conductive layer in turn determines the magnitude and direction of the electrical field within a surface region of the photoresponsive substrate. The magnitude and direction of the electrical field may be monitored by a variety of photoresponsive measurements. The photoresponsive measurements provided a measurement of the redox potential of an unkown electrolyte medium relative to a redox potential of a standard electrolyte, which may be introduced as the electrolyte medium. Multiple photoresponsive measurements may be made sequentially over time, so as to provide information as to the rate of redox potential change of the medium over time.

By employing either a plurality of electrodes or a plurality of irradiation sites on a single electrode, substantial flexibility may be achieved in measuring two or more states of a conductive medium. The states may involve redox potential, pH, concentration of a solute, presence of a particular moiety, volume, temperature, or other variable, which can be detected either directly or indirectly by a photoresponsive electrical measurement.

The device employs light means for interrogating one or more sites of the working electrode. A circuit is provided for determining the signal produced by irradiation of the working electrode, where the signal will be related to the redox potential, the pH, or other ionic components of the medium. These signals in turn may e related to another state of the medium.

The methods employ a wide variety of systems which allow for variation in the redox potential, pH state, or other ionic composition state, of the medium in relation to the state of interest, particularly the concentration of an analyte or the presence of a particular moiety.

The device which is employed may have one or a plurality of working electrodes, each with one or more sites for irradiation, and at least one electronically conductive layer associated with at least one of the working electrodes. Each of the working electrodes will have an ohmic contact or connection to a circuit, where individual working electrodes may have a common connection to the circuit. Alternatiavely, the individual working electrode may have individually switched connections to the circuits, so that each of the working electrodes may be electrically isolated.

Normally, the sample will contact each of the electrodes, and preferably the sample will contact both the electronically conductive layer and the working electrode surface free of the electronically conductive layer. The working photoresponsive electrode may or may not have an insulative layer, but in order to obtain a potentiometric rather than an amperometric measurement, where an insulative layer does not provide the high resistance, the circuit requires some other high resistance element. Hereafter the electronically conductive layer may be referred to as a metal layer, although it should be understood that electron conductors other than metals may also be used.

The measurement of the redox potential, pH, or other ionic composition of the medium are indirect potentiometric measurements, where the photoresponsive parameter, preferably photocurrent or photovoltage, may be measured directly. In this way, if the redox potential, the pH, or the ionic composition is fixed as a reference, by providing for a substantially invariant state of the particular medium components during the period of measurement, the remaining variables may be determined as a function of time. In this manner, a reference electrode, which provides for a standard potential, is not required. Incorporation of such reference electrode, however, allows a separate determination of the medium component of interest to be made. Thus, a variety of physical or chemical states of the medium may be normalized.

Such variables as volume, temperature, solute acitivity, or the like may be determined. For example, a fixed amount of reactant, e.g. enzyme, which produces a known change in pH or redox potential over a predetermined time period in relation to the reference electrode and a prefined set of conditions, can be used to determine a change in one of the conditions, where the other conditions are held constant.

The device will provide for photoirradiation of the working electrode at one or more sites associated with the region under the electronically conducting layer and with the region under an area free of the electronically conducting layer. Photoirradiation may occur simultaneously at both regions, particularly regions contiguous to each other, or sequentially.

For potentiometric measurements, one may employ a ramp in bias potential and measure the photoresponse, e.g., photovoltage or photocurrent, as a function of the bias potential value. Where two or more sites are illuminated sequentially, results of the measured photoresponses versus bias potential relationship are obtained for each site. Where two sites have a metal layer in contact with the electrolyte, a standard redox potential electrolyte may be provided at one, or more, of the sites so as to provide an internal redox potential standard at least one site. The redox potential of an unknown assay medium may be determined at one or more sites that are different from the sites of the standard. The metal layers associated with each independent site may have any shape or form; however, it is important that the metal layers are not connect one to another by any substantially conductive material other than the electrolyte medium.

Alternatively, one or more of the sites associated with the illuminated regions of the working electrode may have the metal layer omitted. In place of the metal layer at these sites a pH-responsive or other specific ion-responsive surface may be provided instead. With this alternative, the pH or other specific ion composition may be maintained fixed at one or more of the sites away from the metal layer so as to provide an altenative internal potential standard. Where the redox potential, pH, or specific ion state of the medium is fixed at one or more sites, any variation in the observed photoresponse versus bias potential relationship can be related to either a change in the state of the medium or to a change in the measurement system. Incorporation of the internal reference standard allows these changes to be determined independently, thereby permitting changes in the measurement system to be subtracted from the observed photoresponse versus bias potential relationship yielding the result of interest. In this manner, one can correct for changes in conditions other than the change of interest.

In carrying out the assay, the assay medium may be prepared by adding the appropriate reagents, which will provide for either a constant redox potential, a constant pH, or other constant ionic moiety composition of a medium during the period of measurement. Where an analyte is being measured, the analyte may be a component of the redox couple, or may react with a component of the redox couple, or may influence the redox potential of a redox couple. Alternatively, the analyte, or a product resulting from the analyte, may affect directly or indirectly the pH or other ionic composition of the medium. Depending upon the particular analyte of interest, the analyte itself may be measured directly or may serve to influence a medium component to provide a change in the observed photoresponsive electrical signal related to the amount of analyte.

In all cases, the electrodes are contacted with the sample, so that the sample forms a conducting bridge between the counterelectrode, the photoresponsive working electrode, and, optionally, the reference electrode. The working electrode is then illuminated so as to produce excess minority charge carriers in a surface region of the photoresponsive substratum of the working electrode where the electrical field is substantially affected by the potential of the metal layer. The electrical signal, i.e., the photoresponsive versus bias potential relationship, may be compared to a standard relationship for a defined set of conditions to determined the redox potential of the medium. One may illuminate, in addition, a region of the working electrode displaced from the metal layer. Excess minority charge carriers in such surface region of the photoresponsive substratum of the working electrode may be produced, where the electrical field is substantially affected by the potential at such site on the working electrode surface. This site may be comprised of an insulator with a pH-responsive surface so as to produce an electric field within a surface region of the photoresponsive substratum that is pH-responsive. Alternatively, either the insulator or base photoresponsive substrate may be coated with a specific-ion-responsive membrane, so as to produce an electric field within a surface region of the photoresponsive substratum that is responsive to a specific ion within the medium. Such ion-selective membranes are well known in theory and operation. See, for example, Steiner, et al., Anal. Chem. (1979) 51:351, and reference cited therein. Ionic analytes of interest include lithium, potassium, calcium, cesium, ammonium, sodium, chloride, fluoride, sulfide, both cations and anions.

The electrical signal, i.e., the photoresponse versus bias potential relationship, may be obtained separately in the redox sensitive region (i.e., the region covered with the metal layer) and in the pH or specific ion sensitive region. These separately obtained signals then may be compared in order to derive a relationship between redox potential and pH or ionic composition of the medium. By repeating both the above measurement and comparison steps over time, one may deduce the rate of change in the relationship between redox potential and pH or ionic composition over time. Because the precision of determining the relationship or rate of change of the relationship is independent of the reference electrode potential, a potential-stable reference electrode is not required for precise measurement of the relationship or rate of change in the relationship over time.

Conveniently, one may illuminate a region of the photoresponsive electrode associated with the border between the metal surface layer and the surface free of such layer. In this event, one obtains a stepped photoresponse upon ramping the bias voltage. The initial step in the photoresponse is related to the potential either of the surface metal layer or the surface free of such metal layer. The second step, is related to the potential of the remaining surface (i.e., the one of the two above surfaces which was not related to the initial step) associated with the illuminated region of the photoresponsive electrode. As long as the initial and second steps are sufficiently separately in applied bias potential voltage so as not to interfere with each other, each of the individual surface potential, or change thereof with respect to time, may be determined. This convenient method offers the advantage of employing only a single beam of illumination and employing only a single ramp in applied bias potential for each multiple determination of surface potentials. The advantages given above for determination of at least two parameters, such as redox potential and pH, for example, are maintained with this convenient and simple method.

The photoresponsive working electrode generally will be composed of semiconductor or photoconductor materials, such as silicon, which may be a single crystal, polycrystalline or amorphous, gallium arsenide, gallium selenide, aluminum gallium arsenide, chlorogallium phthalocyanine or the like. The semiconductor material will be either of the p- or n-type and, as appropriate, and may employ such dopants as boron, aluminum, phosphorus, arsenic, antimony, or the like. The degree of doping may be varied widely, there being a wide variety of commerically-available doped wafers which can be used, where by body of the wafer is lightly doped and portions of the wafer heavily doped. The doping will be substantially uniform adjacent to the surface in contact with the sample. There also are available arrays of individual microchips which are insulated one from another which may be joined to a common circuit with or without switching elements connecting the individual chips to the circuit. The concentration of the dopant normally will vary empirically to provide the desired response, frequently being a matter of convenience, and generally will range from about $10^{12}$ to $10^{18}$ atoms/cc, usually for silicon, the resistivity will be about 0.01-1000 ohm-cm.

Where the monolithic wafers are used, they may come in a variety of sizes and shapes, varying from chip size which may have its largest dimension of at least about 1.0 mm, usually 2mm; or wafer size, which may be 500 mm, more usually not more than about 100 mm in its largest dimension. The electrode region usually will have at least one smooth surface of smooth portion of a surface, desirably flat, which will serve as the electrode surface. The wafer may be round, rectangular, elongate or the like. The thickness of the chip or wafer generally will be not more than about 2 mm, usually less than about 1 mm, and generally not less than about $0.05\mu$, usually not less than about 0.1 mm.

An insulative layer normally is employed to cover the exposed working electrode regions, which layer usually will be coated uniformly. The significant factor is that the semiconducting portion of the working electrode is insulated electrically and chemically from the medium by some means. Conveniently, a coating of silicon oxide and/or silicon nitride can be employed, generally of from about 200 to 2000Å, preferably from about 600 to 1500Å to provide for the insulative layer. The silicon oxide or nitride can be used by itself or in conjunction with other materials, or such other materials may be used substantially independently of the silicon oxide or nitride. That is, various insulative coatings may be employed which are stable under the conditions of use and provide for the desired degree of insulation and response.

Depending upon the nature of the insulative coating and the manner of attachment to the surface, various techniques may be employed for providing the coating. Methods for providing coatings include spraying, painting, dipping, reacting with an active vapor, e.g., steam or ammonia, or a reactive reagent in solution, e.g., silyl chloride, vapor deposition, electrodeposition, or the like.

Silicon oxide layers can be achieved with the use of oxygen or water vapor, controlling the thickness of the layer by the conditions employed, e.g., time and temperature. Silicon oxide coatings also can be obtained by electrodeposition. Silicon nitride layers can be obtained by reaction of silicon and nitrogen or reaction of compounds containing silicon and nitrogen such as dichlorosilane and ammonia. Standard methods of deposition of silicon nitride from the reaction of silanes and ammonia or nitrogen in the gas phase are well known to those skilled in the art of microfabrication.

The device may have a single continuous surface ranging from a surface area of about 1 $mm^2$ to about 250 $cm^2$, more usually about 5 $cm^2$, but in most instances will be a plurality of individual elements insulated from each other, so as to provide for independent signals to the same circuit. The individual units generally will range from about 0.1 $mm^2$ to 25 $mm^2$ or greater, the upper limit being primarily one of convenience, and the effect of size on sensitivity.

The individual units may be in contact with media which are isolated partially, or completely, from each other by the presence of partitions which allow for electrical communication, for example, membranes, porous walls or partitions extending only a partial distance to the surface, or by insulated partitions which inhibit any electrical communication between the partitioned media.

The surface of the device may be divided up physically in a variety of ways, providing for compartments, which may be of any convenient periphery, circular, square or the like, channels, which may be circular, serpentine or straight, or combinations thereof. Extended areas such as channels allow for inspection of a moving solution at different times. Channels can be provided by having grooves in either the redox potential, pH, or specific-ion-selective surface of the working electrode or the opposing surface. Compartments can be divided by having indentations in either of said surfaces. The number of independent units to be measured may be 1, 2, or more, usually 3 or more, and may be 50 or more, and could be as high as 500 or more.

In fabricating the device, individual semiconductor elements may be employed, arrays of such elements or a monolithic semiconductor, where the photoresponsive substrate, e.g., the semiconductor, may be substantially uniform or homogeneous in composition in the region of interest or individual areas ("pixels") may be isolated by various mechanical (structural) or electrical means.

When a monolithic semiconductor wafer is used as the photoresponsive working electrode, a number of isolated electrode regions (hereinafter referred to as "pixels") may be formed by doping certain locations, which are separated from other electrode regions by insulating regions. Individual pixels (electrode regions) are coupled to a circuit which provides a ramped DC bias voltage applied between the working electrode and the reference or controlling electrode, so as to produce a measurable photoresponse as a function of the applied DC bias potential. Alternatively, the DC bias voltage may be applied to maintain the photoresponse at a fixed or known value and DC bias potential required to maintain the fixed or known value is recorded. In one method of operation, the redox potential-sensitive region of the working electrode (i.e., the region associated with the metal surface layer) and a region associated with either the pH-sensitive surface or other ion-selective surface are illuminated simultaneously. The illumination intensity is made to vary with time so as to produce a time-varying response such as photocurrent or photovoltage (e.g., an alternating photocurrent or photovoltage). The amplitude of the alternating photocurrent, photovoltage, or other photoresponse may be determined by at least the following potentials: the applied bias potential, the potential of the metal surface layer, the potential of the pH sensitive surface, or the potential across an ion-selective membrane. As long as the amplitude of the alternating photocurrent, photovoltage, or other photoresponse changes in separate and discernible steps as a function of the applied bias potential, the effects of changes in redox potential, pH, or other selected ionic composition of the medium may be determined separately. In the course of an analyte assay procedure, such a change may be realized by changing the assay medium from a standard composition to a second, or unknown, composition or by introduction of an enzyme or other catalyst which causes the redox potential, the pH, or another selected ionic composition of the electrolyte medium to vary with time.

A plurality of pixels can be provided with a single photoresponsive electrode by insulating each of the pixels frm each other. Such electrical insulation may be effected either by interposing nonconducting material between pixels (insulator isolation) or, when the photoresponsive material is a semiconductor, by applying a reverse-bias potential to a p-n semiconductive junction (junctional isolation). The techniques employed in fabrication of such electrically insulated regions in a single monolithic semiconductor crystal, in particular, are well known to those skilled in the art of semiconductor microfabrication. See, for example, I. Brodie and J. J. Murray, *The Physics of Microfabrication*, Plenium Press, New York, 1982; and S. M. Sze, *Physics of Semiconductor Devices*, 2nd Edition, Wiley-Interscience, New York, 1981. Alternatively, one may separately construct individual photoresponsive working electrodes, as described above, and place a multiplicity of these electrodes on or in a matrix of material which effectively electrically insolates the electrodes from one another.

For measurement of changes in the photoresponsive working electrode potential, an external measuring circuit will be utilized. The circuit, or multiplicity of circuits, may make electrical contact, separately, with each of the pixels. In the case of a single circuit, separate electrical contact with each of the pixels is made in temporal sequence by means of an electrical switching mechanism. Additionally, the external circuit(s) makes contact with either a single counterelectrode or a multiplicity of counterelectrodes placed in the liquid sample medium.

In the embodiment where the semiconductor electrode is comprised of a plurality of pixels, the pixels can be fabricated individually or be part of a single semiconductor wafter. The semiconductor wafer then may be doped oppositely from the dopant of the wafer at a plurality of sites to define the pixels (junctional isolation). Various means may be provided for ensuring the insulation of each of the pixels from each other. A reverse-bias potential (voltage) may be applied to the oppositely doped region in order to insure that the p-n junctions are maintained in their nonconducting (reverse-biased) state. Ion or charge implantation in the region of the p-n junction may be used as another means of insuring that the junctions are maintained in the nonconducting state. Alternatively, the immediately surrounding area of each pixel may be eroded, so as to create a well between each pixel and the resulting islands and intervening areas modified to provide for an insulative region. The insulative region may be an oxide or nitride or a combination thereof, or another ceramic insulative material such as alumina, a glass, or quartz. Polymers of nonconducting organic material may also find use. A vast variety in such materials exist including, epoxides, polyamides, polyacrylates, polyolefins, and polyfluorocarbons. Each of the pixels may have an independent contact to a circuit, so that any change in the electrical measurement may be determined individually or may have a common lead to a circuit. Various techniques can be employed for connecting the pixels individually to the external circuit.

Various electrical circuits may be used to measure changes in photoresponsiveness of the working electrode as a function of the applied bias potential, which results from changes in the state of an individual portion of the medium. These electrical circuits may measure primarily changes in photoconductance, photovoltage, photocapacitance, or photocurrent. The circuits will be chosen so as to provide maximal sensitivity for detecting small changes in the state of the parameters. These measured parameters generally will be referred to as the photoresponse.

The observed signal from the circuit can be a result of a change in direct current, alternating current or the effect of a direct current on an alternating current.

The circuits employed allow for measuring different variables, such as AC amplitude, bias potential, DC amplitude, the AC component of the light intensity amplitude, the DC component of the light intensity amplitude or the like. The variables can be interrelated automatically by varying the bias potential or light intensity relationship to the photoresponse. For example, one can vary the bias potential to maintain a constant AC or DC photoresponse and measure the required change in bias potential, or one can fix the bias potential and measure the direct current resulting from steady illumination or the alternating current resulting from amplitude modulated illumination; or, one can fix the amplitude of the AC or DC phtoresponse by varying the intensity of the modulated or continuous illumination and measuring the required light intensity.

As to each of the pixels, there will be an electrically conductive layer, usually a coated metal layer upon an insulative layer of the working electrode. The electrically conducting layer may be applied to the surface of the working electrode in a variety of ways, inlcuding sputtering, ion beam or thermal evaporative coating or by other vapor deposition methods, by electrodeposition, or by precipitation. The electrically conducting layer will generally be of a thickness in the range of about 5Å to 5 mm, more usually in the range of about 0.01 to 10$\mu$. The surface area of the electrically conducting layer is not critical above a certain minimum, generally having a surface area of at least about 1$\mu^2$ more usually at least about 1 mm$^2$, and preferably from about 1 mm$^2$ to 20 mm$^2$.

As to each of the pixels, where each pixel has its own electronically conducting (e.g., metal layer) region and pH sensitive region, the pH sensitive regions of specific-ion-sensitive regions will have a surface area of at least about 10$\mu^2$, usually at least about 1 mm$^2$ to 100 mm$^2$.

The materials employed for the electrically conducting layer for the redox site will be selected so as to be inert to the medium and adherent to the substratum, to have electrically conducting properties of or, analogous to metals, be capable of being coated onto the working electrode surface and to be readily controllable as to placement, thickness and the like. For the most part, the noble metals will be employed, such as gold, platinum, rhodium, iridium, or the like. However, other materials may be employed, such as highly doped semiconductive materials, both organic or inorganic, e.g., graphite, tin oxide, indium oxide, or mixtures of tin an indium oxide.

The subject devices can address one or more incremental portions of one or more media to be analyzed, where the incremental portion or volume can be indicative of the gross properties of the medium or particular incremental portions of the medium, where properties of incremental portions may differ in their properties one from the other as well as from the properties of the gross medium. One can interrogate specific sites or pixels by illuminating an individual site and determining the electrical signal resulting from the individual illumination or illuminate all the pixels simultaneously, using one or more sources of illumination, where the pixels are independently connected to the circuit. To direct light to specific areas, individual light sources may be directed by lenses or light directing means to the site, e.g. optical fibers, or a common light source with masks, optical filters, or the like may be used. In this way, one can address different portions of the medium to determine the state of the incremental portion as to its redox potential, pH or other ionic composition, and determine variations in the state of the medium over a large volume.

Furthermore, one may employ one or more channels and determined the state of the incremental portions along the channel, so that one can relate variations in the states of the incrmental portions along the channel to a temporal change occurring in the medium. By using continuous or intermittent flow techniques, or by mixing two media which provide for a detectable reaction prior to entering the channel, one can provide a steady state at different sites along the channel. In this manner, one can determine rates of reaction by observing the steady state properties of the medium at different sites along the channel.

The counter- or second-electrode generally will be at a position from about 0.01 mm to 5 cm distance from the insulative layer, more usually from about 0.1 mm to 10 mm. The counterelectrode may be any conducting or semiconducting material, such as metals; e.g, platinum; gold, titanium, stainless steel, brass or other conducting oxides, e.g., indium-tin-oxide; doped or heavily doped semiconductive materials, e.g. silicon; conducting polymers, e.g. polypyrrole; or the like. The second electrode desirably will be of a material which is inert to the sample medium or will be coated with a protective layer, which may be a thin film, generally under about 5 mil, usually under about 1 mil, which may be an organic polymeric layer, a silicon oxide or nitride layer, or the like. Alternatively, the protective coating may be comprised of a series of such layers. Depending upon the photoresponsive or first electrode, the second electrode will be either a point or a continuous electrode facing the operating surface of the first electrode or will be a plurality of individual electrodes associated with individual sites of the operating area of the photoresponsive electrode.

The counterelectrode may assume a number of conformations. The counterelectrode may be a wire, a thin layer on a support, being present as stripes, dots or a continuous coating, may be a metallic or semiconductor layer or wafer.

Each working electrode will have a connection, either individual or common, through ohmic contact to a circuit for detecting changes in a medium component. Where a monolithic photoresponsive wafer is employed having a plurality of medium-contacting regions, only a single lead is required to the working electrode.

Irradiation of the photoresponsive substrate may be from either side of the wafer. However, where the irradiation occurs on the side opposite to the side associated with the medium of interest, it will be necessary that the wafer be thin, so that the conductive band which is influenced by the medium of interest can also be affected by the light irradiation. Normally, in this situation, the thickness of the photoresponsive element will be from about $0.05\mu$ to 5 mm, usually from $10\mu$ to 1 mm.

The light source may be any convenient source, particularly of photon energy at least about the conduction band gap of the photoresponsive substrate, so as to produce mobile charges, i.e., free electrons and positive holes: For silicon, this is about 1.1 eV. The light source generally will vary in the range of ultraviolet to infrared. This would provide for a wavelength range generally in the range of about $0.1\mu$ to $1\mu$, more usually from about $0.3\mu$ to $1\mu$. Other photoresponsive materials can be matched with a light source accordingly. By employing phosphorescent or chemiluminescent dyes as a thin layer on the illuminated working electrode surface, higher photon energy light may be employed to stimulate emission of layer photon energy light by a phosphorescent or chemiluminescent processes. The light and dark periods for pulse radiation may be the same or different, generally ranging from $10^{-2}$ to $10^{-6}$ seconds. The total time of irradiation of a particular site is not critical and may range from $10^{-3}$ to 100 seconds.

Any source of light may be used which provides the means for providing continuous or intermittent light for short periods of time, particularly a source which can provide for cycling the light at a predetermined frequency, e.g., 100 Hz–100 Hz, usually 100 Hz–50 kHz, more usually 1–20 kHz, during the period of irradiation. Of particular interest are LED arrays, which are available for providing red light, or a tungsten lamp or other light source for white light. Alternatively, a single source can be used, e.g., fluorescent light in the visible region, where shutters are used, nematic liquid crystals, gratings, optical fibers, choppers, or the like, may also find application.

In the absence of individual connections for the pixels, the different sites will be irradiated at different times to provide a simple method for distinguishing between the signals associated with the individual sites. However, simultaneous irradiation of different sites may be employed, where a means is used to allow for distinguishing the signals, such as a phase shift, alternating frequencies, or other combinations where the signals can be segregated.

Various circuits may be employed for determining the state of medium component. With a semiconducting working electrode, and in the case where the circuit provides for forward bias (majority charge carrier accumulation) at each redox potential site, pH sensitive site, or other specific-ion detection site, no signal will be observed. Where one site is reverse-biased (minority charge carrier depletion) and the other site forward-biased, one will observe only the signal resulting from the site which is reverse-biased. Where two sites are reverse-biased, one will observe the signal from two sites, and so on. Where there is a common connection between all of the working electrodes and the circuit, the circuit is coordinated with the photoilliumination, with the observed signal being related to the number of photons impinging at the site up to the saturation level. The circuit will include a potentiostat to provide for a controlled potential, so that readings may be performed by determining the required voltage to restore the photopotential, photocurrent, or other photosignal of the working electrode as it varies in response to changes in the sample medium.

Because of the diversity of redox materials which can be detected, the permissible variations in the conformations which can be employed, and the flexibility in circuitry, a wide variety of different systems and situations can be addressed by the subject invention. While for the most part, fluids providing for modulation of a photoresponsive electrical signal will be monitored, the subject invention allows for monitoring of solids and semi-solids in appropriate situations. Thus, a large variety of reagents and combinations of reagents may be used as a redox, and/or pH, and/or other specific-ion-modulating system.

The subject invention can be used for monitoring various streams, such as effluents, natural bodies of water, industrial streams from chemical processing plants, refineries, power generation and the like, air, or other fluid, where the fluid has component which will affect a photoresponsive electrical signal or such component can be employed in conjunction with other materials to provide for such a response.

A photoresponsive working electrode can be influenced by the redox potential of the medium adjacent to the surface of the electrode. Various redox systems can be employed which can be in vitro or in vivo systems involving cells, e.g., microorganisms, mammalian cells, etc., enzyme reactions, particularly oxidoreductases, e.g., glucose oxidase, peroxidase, uricase, NAD or NADP dependent dehydrogenases, naturally occurring electron transfer agents, e.g., ferridoxin, ferritin, cytochrome C and cytochrome $b_2$, organic electron donor and acceptor agents, e.g., methylene blue, nitro blue tetrazolium, Meldola blue, phenazine methosulfate, metallocenes, e.g., ferrocenium, naphthoquinone, N,N'-dimethyl 4,4'-dipyridyl, etc., and inorganic redox agents, e.g., ferri- and ferrocyanide, chloronium ion, cuprous and cupric ammonium halide, etc.

Various oxidoreductase enzymes may provide or be coupled to a redox couple. Enzymes which may be coupled with NAD/NADH or NADP/NADPH include alcohol dehydrogenase, glutamine dehydrogenase, malic dehydrogenase, isocitric dehydrogenase, α-glycerolphosphate dehydrogenase, glyceraldehyde-3-phosphate dehydrogenase, glucose-6-phosphate dehydrogenase, glutathione reductase, quinone reductase, cytochrome C reductase, D-amino acid oxidase, L-amino acid oxidase, peroxidase, ascorbate oxidase, pyridine nucleotide reductase, hydrogenases, etc.

Various enzymes may be employed to provide for changes in pH. For the most part, these enzymes will by hydrolases used by themselves or in conjunction with oxidoreuctases. Illustrative enzymes include esterases, phosphatases, pyrophosphatase, sulfatases, proteases, sacccharidases, or the like. The change in pH may be as a result of production of anions which are the salts of acids, such as phenolates, carboxylates phosphates, etc, or cations which are the salts of bases, such as ammonium or neutral acid-generating or neutral base-generating species such as carbon dioxide or ammonia. The enzyme urease, which produces carbon dioxide and ammonia from urea, in particular is an enzyme well suited for this use.

In one embodiment, one could monitor the change in biological oxygen demand or chemical oxygen demand of an effluent stream or river by having a plurality of channels which can devide up the stream into numerous individual channels, where different chemicals could be introduced into each individual channel, where the chemical or the product of the reaction provides for modulation of the photoresponsive electrical signal. Where there is a change in the redox potential, the rate of change can be determined by determining the change in electrical signal at defferent sites along the channel and relating the rate to the chemical or biological oxygen demand.

One can use the subject device for measuring rate of reactions, such as enzymatic reactions, where the enymatic reaction results in a change in redox potential or pH of the medium. This can be done in a dynamic or static way in that by employing a moving stream, one can make the rate determination substantially instantaneously. Alternatively, by having a relatively static solution at a particular site, which is irradiated intermittently, and readings taken at different times, one can also determine the rate. The device may be used to determine the enzyme-catalyzed rate of reaction, where the enzyme catalyzes reduction of excess substrate using electrons generated by the working electrode. In such cases, rate of reduction (and hence concentration of enzyme) determines the direct current flow at the surface of the working electrode (and hence the change in the measured photoresponse). In such cases (e.g., as for horseradish peroxidase), enzyme concentration may be measured over a period as short as 1 to 5 seconds.

The subject invention also can be used with semi-solid or solid media, employing appropriate adaptations. For example, chromatographic layers, gels or the like, can be used where a redox signal is associated with a component of interest, where a mixture has been separated into components by thin layer chromatography, electrophoresis, density gradients, etc.

Of particular interest will be the use of the subject invention in detecting the presence of a specific component of a medium, where the component may be a chemical, either synthetic or naturally-occurring, such as drugs, hormones, proteins, steroids, receptors, nucleic acids, or the like; or aggregation of chemicals, such as nucleosomes, viruses, cells, both prokaryotic and eukaryotic, or the like. These determinations frequently will be made in physiological fluids, such as blood, plasma, saliva, cerebral spinal fluid, lymph, urine or the like.

In some cases, such determinations will involve a combination of a ligand and receptor, where the ligand and receptor have a specific affinity, one for the other, so that they provide a pair of specific binding members. Receptors for the most part will be antibodies, enzymes, or naturally-occurring receptors, e.g. surface membrane receptors, and can for the purposes of this invention include nucleic acids, while ligands may be any compound for which a receptor is available or can be made.

One could analyze for DNA or RNA sequences, e.g., alleles, mutants, recombinants, etc., by having labeled oligonucleotide sequences which label provides for a redox reaction or pH change. For example, one could bind DNA or RNA probes to a glass surfaces with different oligonucleotide sequences at different sites. The DNA or RNA sample would be prepared by denaturing any double-stranded polynucleotide, e.g., dsDNA, and mechanically, e.g., shearing, or enzymatically, e.g., one or more endonucleases, providing an averagesized fragment ranging from 500nt to 20knt. The sample then would be mixed with labeled sequences which homoduplex with the bound oligonucleotide sequences, so that the labeled sequences compete with the sample sequences for the bound sequences under hybridization conditions of a predetermined stringency.

After allowing sufficient time for the homologous sequences to become bound to the glass surface through the intermediacy of hybridization to the bound sequence, the slide is removed, washed and placed in juxtaposition to the photoresponsive working electrode, where a solution between the two surfaces provides for a redox reaction or pH change with the label.

The systems involving specific (receptor-ligand) binding pairs may be varied widely and may involve a "homogeneous" systems, where there is no binding to a solid surface, or a "heterogeneous" system, where there may be binding, which binding is renewable or non-renewable. By "renewable" is intended that one can remove an active component of the assay system from the surface and replace it with another component.

For the most part, an aqueous buffered medium will be employed, which may be from very lightly to heavily buffered, depending on the nature of the material generating the signal and whether the redox medium also is used as the buffered standard medium or the redox system is used as the constant system. Various buffers may be employed, such as carbonate, phosphate, borate, tris, acetate, barbital, Hepes or the like, at concentrations in the range of about 0.001 to 0.5M. Organic polar solvents, e.g., oxygenated neutral solvents, may be present in amounts ranging from about 0 to 40 volume percent, such as methanol, ethanol, 1-propanol, acetone, diethyl ether, etc.

In the specific binding pair assays, there will be a label conjugated to a substance, where the modulation of the photoresponsive signal will be related to the amount of analyte in the sample being assayed. The substance may be the analyte, analyte analog, the complementary binding member or a substance binding to any of these substances. Such substances include antibodies to the immunoglobulin of a species, e.g., sheep antibody to murine immunoglobulin. Also included are pairs, particularly hapten-receptor pairs, where the substance is modified with a hapten, e.g., biotin, and a reciprocal labeled binding member, e.g., avidin. Thus, the label may be bound directly or indirectly, covalently or non-covalently, to a member of the specific binding pair which includes the analyte. A system is employed which may have one or more components which provides a redox material in relation to a photoresonsive site and which modulates, directly or indirectly, the photoresponsive electrical signal and/or produces or destroys an acidic or basic compound, modifying, cleaving, or producing a neutral compound. A substantial diversity of modulating materials may be employed in the specific binding assays, which materials may be the result of a catalyzed reaction, e.g., an enzyme catalyzed reaction.

For the homogeneous system, it will be necessary only that binding results in modulation of an assay system which results in the redox and/or pH modulation of the photoresponsive electrical signal. The binding can occur adjacent to the surface of the photoresponsive working electrode or distant from the surface, where the surface can be used later to determine the level of the detectable compound in the assay medium. For example, one could carry out a plurality of assays in separate containers, e.g., microtiter plate wells, where the redox potential and/or pH of the medium is changed in each of the wells in accordance with the amount of an analyte. One then simultaneously or serially could transfer aliquots of each of the sample media to individual compartments having the photoresponsive working electrode surface as the floor of each of the compartments. Either each compartment will have one or more additional electrodes acting as a controlling or reference electrode, or alternatively an ionically conducting salt bridge is placed between the individual compartments. The individual samples then would be screened by illuminating each compartment in turn and determining the signal associated with the irradiated sample medium. Alternatively, the monitoring of the assay reactions could be carried out with the photoresponsive surface at the bottom of the separate container employed originally as the reaction chamber, e.g. microtiter plate wells. As in the previous case, each compartment must have at least a second electrode acting as either a reference or controlling electrode or an ionically conducting path is placed between the individual containers. Each well may have additional electrodes, preferably each having the photoresponsive working electrode, a reference electrode, and a controlling electrode. Or, the assay could be carried out adjacent to the photoresponsive surface, by having a number of partial partitions extending only a portion of the distance through the assay medium and introducing the sample adjacent to the photoresponsive surface. Because the rate of formation of the detectable product will vary with the amount of analyte in the compartment, by comparison of differences between compartments having known amounts of analyte and compartments containing the sample, one can relate the result from an unknown compartment to the standards.

Homogeneous assays include such assays as described in U.S. Pat. Nos. (label) 3,817,837 (enzyme); 3,935,074 (any ligand); 4,160,645 (nonenzymatic catalyst); 4,192,983 (liposome); 4,208,479 (enzyme modifier); 4,275,149 (particles); and 4,341,865 (suicide inhibitors), which appropriate parts are incorporated herein by reference. These patents involve enzymes, redox reagents, and combinations thereof:

For example, there is a commercial assay sold under the trademark EMIT. The assay employs the enzyme glucose-6-phosphate dehydrogenase, which produces NADPH from NADP. The photoresponsive electrode may be used to measure the ratio of NADPH:NADP concentrations. The rate of enzymatic reaction may be determined from the measured rate of change in their ratio provided that the initial concentrations of both NADPH and NADP are known. Alternatively, a standard calibrating enzyme or standard analyte reagent may be used to standardize unknown concentrations of NADPH and NADP for the determination of either enzymatic rate or analyte concentration, respectively. Similarly, other enzymes that reduce (or oxidize) NADP (NADPH) or NAD (NADH) may be detected and the enzymatic rate quantitated. The reaction of NADH and NADPH at metal electrodes is well known (Blaedel and Jenkins, *Anal. Chem.* (1975) 47:1337–1343; and Cunningham and Underwood, *Arch. Biochem. Biophys.* 117:88–92). In order to measure the ratio of reduced and oxidized pyridine nucleotides potentiometrically, however, it is necessary to provide a redox catalyst, e.g. phenazinemethosulfate, Meldola blue, dichloroindophenol, or the like. This potentiometric method for detection of pyridine nucleotide enzymatic cofactors provides substantial advantages over amperometric methods of detection because amperometric methods are sensitive to interference due to adsorption of protein onto the metal electrode. No such interference has been found with the present potentiometric method for determination of redox compounds.

The EMIT$^R$ homogeneous enzyme assay employs antibodies to an analyte where the analyte or an analyte analog is bound to the enzyme to provide an enzyme-analyte conjugate. When antibody to the analyte binds to the enzyme-analyte conjugate, the enzymatic activity is substantially diminished. Thus, the rate of formation of NADPH can be determined and related to the amount of analyte present in the volume adjacent to the photoresponsive site.

In carrying out the assay, one could have the photoresponsive site with a plurality of partial partitions defining a plurality of compartments where the assay medium extends beyond the partitions and makes connection with a second or a second and third electrode. The assay medium would include the enzyme conjugate, buffers, stabilizers, and other additives, which are not directly involved in the system providing for the detectable signal. One would prepare a sample solution containing the antibody, the sample, and appropriate substrates, the mixture incubated, and then injected into the appropriate compartment. The rate of production of either a redox reagent, pH changing agent, or other specific-ion concentration changing agent, could be followed as indicative of the amount of analyte present in the sample.

Alternative to conjugation of either analyte or reciprocal binding pair member to an enzyme, one could conjugate analyte or reciprocal binding pair members to substrates, co-factors, suicide inhibitors, or the like. Various of these techniques are disclosed in U.S. Patents described above. Therefore, one could prepare a conjugate comprising a suicide inhibitor and an analyte. One could bind enzyme, either covalently or non-covalently, to a surface, either the photoresponsive surface or a surface adjacent to the photoresponsive surface. A sample solution would be prepared of antibody to the analyte, the sample, the suicide inhibitor conjugate, substrates, and any additional reagents necessary for producing a detectable product. One then could add the sample solution to the enzyme bound to the surface and determine the enzyme activity.

The heterogeneous system allows for separation between complexes between specific binding pairs and uncomplexed specific binding pair members. This is achieved by having one of the members of the specific binding pair bound to a solid surface. One could prepare a clear slide having specific antibodies at different sites on the slide, so that one could assay a sample for a plurality of analytes. One would then add antibodies for each of the analytes to the solution, so as to employ a sandwich immunoassay. Conveniently, the antibodies would be monoclonal antibodies to minimize cross-reactivity. One would then add a solution of an enzyme-antibody conjugate where the antibody binds selectively to immunoglobulins from a particular species. For example, if the monoclonal antibodies ae murine, one could conjugate rabbit antibodies specific for murine immunoglobulin with a suitable enzyme which provides for a redox reaction, e.g., glucose oxidase or peroxidase; or a pH change, e.g., alkaline phosphatase, urease or acetyl cholinesterase. Thus, only where the monoclonal murine antibody had bound, would there also be enzyme conjugate. One would then place the slide adjacent to the photoresponsive surface in registry, so as to define where each of the original antibodies were. A thin, liquid film at the surface would provide the appropriate reagents and substrates for reaction with the enzyme to produce the detectable event.

One then would irradiate sequentially sites on the photoresponsive working electrode to determine whether any enzyme had become bound at a particular site. Each site would have either a separate or a common counterelectrode. In this manner, a sample could be assayed for a large number of different analytes, substantially simultaneously to provide for a complete battery of determinations on a single sample, where extremely small amounts of the sample would be required.

Heterogeneous techniques are described in U.S. Pat. Nos. 3,654,090 (enzyme); 3,791,932 (enzyme); and 4,134,792 (enzyme substrate), which patents are in appropriate part incorporated herein by reference.

If one wished to use repeatedly the same surface, one could apply a member of a specific binding pair to the surface, where the complementary member is conjugated to a member of a specific binding pair related to the analyte. For example, one could coat the surface with the same or different sugars, haptens, receptors, antibodies, or members of naturally occuring ligand-receptor pairs. One then would conjugate the member of the specific binding pair related to the analyte to the binding member complementary to the material bound to the surface. To illustrate, one could coat the surface with a saccharide and conjugate the analyte related specific binding pair member, e.g., antigen, to a lectin. Thus, one could prepare conjugates of antibodies and protein analytes or lectins. By adding a solution of the antibody-lectin conjugate to the saccharide-coated surface, the antibodies would become bound to the surface. One could then carry out the assay as described above. After completing the assay, one could regenerate the surface for repeated use by removal of the complexed material from the surface by adding a concentrated solution of the saccharide. One can use other pairs by analogy, where in place of a lectin, an antibody or natural receptor could be employed. Thus, a single surface can be used which could be replenished repetitively so that the same or different types of assays may be employed after each determination. By binding different compounds to the surface at different sites, one can direct specific binding pair members to a specific site with the appropriate conjugate.

Various techniques may be used with enzymes for amplification and enhanced sensitivity. One may employ enzymes which require co-enzymes or substrates which can be produced by another enzyme, the interaction between the enzymes referred to as "channeling." For example, one could bind a first enzyme to the slide and have the second enzyme conjugated to the receptor. Thus, the first enzyme could provide for a localized high concentration of the substrate or co-enzyme for the second enzyme. Illustrative enzyme pairs include glucose oxidase and horseradish peroxidase, which can act to oxidize or reduce an electron transfer compound, hexokinase or glucokinase, and G6PDH, which with glucose, ATP and NADP can produce NADPH, which then can be detected in the presence of a redox catalyst by the metal redox responsive layer on the photoresponsive working electrode. The rate of change in the redox potential or the instantaneous redox potential could be related to the presence of an analyte.

Catalysts, particularly redox catalysts, may be employed in lieu of enzyme catalysts, either completely or in part. These catalysts may include such compounds as phenazine methosulfate, methylene blue, nicotinamide adenine dinucleotide (NAD), Meldola blue, flavin mononucleotide, ferri- and ferrocyanide, and the like. These compounds may be used in conjunction with enzymes or other catalytic compounds to provide for a redox potential or current flow at the photoresponsive surface. For example, instead of conjugating one member of a binding pair to an enzyme, one could conjugate to a redox catalyst such as phenazine methosulfate, Meldola blue, methylene blue, etc. Then by capturing the conjugate at the redox-sensitive, photoresponsive, working electrode surface, a modified redox signal would be produced at the photoresponsive redox-sensing electrode upon introduction of substances, which accept or transfer electrons relative to the redox catalyst.

Redox reagents can be coupled with naturally occurring enzyme transport systems involving cells membrane fragments, or the individual members may be joined in vitro or dispersed independently in the medium. Thus, amplification can be achieved. Alternatively, the presence of intact cells or cell fragments can be detected by their influence on a redox couple. For example, methylene blue may be added to a medium suspected of containing microorganisms, e.g., bacteria, which are chemically reductive. Reduction of the methylene blue can be detected rapidly as indicating the presence of reductive microorganisms.

In many situations it will be of interest to determine the presence of a natural receptor in a physiological fluid, particularly blood or plasma. Usually, the receptor will be an antibody, resulting from an autoimmune disease, foreign substance, or an infection. The antibody may be detected in a competition assay, where the endogenous antibody competes with labeled antibody for the complementary antigen or the antibody may serve as a bridge to bind labeled antigen to antigen bound to a surface or particle. Otherwise, for the most part, the antibody assay would follow the techniques employed for detecting antigens.

One of the advantages of the subject invention is that it may use chemistries developed for use with spectrophotometric or fluorometric detection systems. For example, biotin-modified nucleic acids are described for use as probes. By coupling an appropriate enzyme to avidin, one could probe a DNA or RNA sample fixed to a surface with the biotin-modified probe under stringent hybridization conditions. After removal of non-specifically-bound probe, one would add the avidin enzyme conjugate and additional members of the redox system. For example, the enzyme lactate dehydrogenase may be employed as the label, and either lactate or pyruvate as substrate; and NAD and NADH employed as cofactor. Depending on the nature of the photoresponsive surface, one could detect the change in the NAD/NADH ratio. Alternatively, the coenzyme, in this case nicotinamide adenine dinucleotide, could be coupled to a second redox couple, e.g. ferri-/ferrocyanide, and the rate of change in the redox potential of the second redox couple could be related to the amount of enzyme present. As yet a third alternative, a coenzyme could be used as a label such as FMN, FAD, or NAD which could be coupled with an enzyme and a second redox couple, where the rate of transformation of the second redox couple would be related to the amount of coenzyme present. As a fourth alternative, a sample containing a plurality of microorganisms may be spread on an appropriate nutrient agar gel and cloned. Employing the Grunstein-Hogness technique, cells are transferred to a nitrocellulose porous film in appropriate registry with their position on the gel, lysed and the DNA fixed to the film by heating. Probes having a complementary sequence to a unique sequence of the organism of interest are provided as partial single strands with a double-stranded 3'-terminus having a sequence specifically recognized by a specific binding receptor, e.g., repressor, rho, N protein or lambda, or the like. The film is contacted with the probe under hybridizing conditions, e.g., 50% aqueous saline: 50% dimethyl formamide and the hybridization solution then removed. After washing the film, a solution is added containing a specific binding receptor labeled with an enzyme which catalyzes a reaction which modifies the redox potential or pH of the medium. After allowing sufficient time for the labeled protein to bind, the film is washed free of nonspecifically bound protein and placed in close-facing juxtaposition to the photoresponsive working electrode. The enzyme substrate is then added and the signal from the system determined.

The microorganisms also can be used to measure the presence of a biostat or biocide in a medium. By combining the medium with growing microorganisms and determining the rate of growth of the microorganisms as compared to a standard differing only in the absence of the medium, the presence of a biocide can be detected. By employing immortalized mammalian cells, e.g., tumor cells, the presence of growth regulators also can be detected.

The following examples are illustrative of the manner in which the subject methodology could be used. The device, either a single surface or a plurality of individual non-contiguous surface units, has paritions to isolate individual volumes or compartments. A film is employed proximate to the surface having lectins specific for a particular mono- or oligosaccharide. Antibodies against the same or different ligands are modified with the particular saccharide and are introduced into each compartment and the excess washed away. A sample is now introduced which overflows the compartment partitions and any complementary ligand becomes bound in the appropriate compartment. The sample is then washed away and an antibody mixture is added which binds to the single or multiple ligand bound to the antibodies in the compartments. The antibodies added in this latter step are all from a single source, e.g., mice, whereas the saccharide modified antibodies used in the earlier step are not from this source. The mouse antibody solution is washed away, a conjugate of an enzyme, for example, with rabbit antibody to mouse immunoglobulin is added and allowed to overflow the compartment walls and bind to any mouse immunoglobulin in the compartments. The nonspecifically-bound enzyme then may be washed away and the enzyme activity in each compartment is determined by adding a substrate medium to each compartment which provides a product which can be determined photoresponsively.

In another embodiment, individual photoresponsive units are provided having anti-analyte antibodies covalently bonded to the surface of each unit through a silyl-substituted aliphatic carboxylic acid. The analyte-containing sample is then introduced to the antibody-modified surface, the sample washed away and enzyme-conjugated anti-analyte sandwich-forming antibody added. After sufficient time for binding, nonspecifically-bound enzyme is removed and a developer solution added. The enzyme may produce a pH change, redox potential change, or a change in concentration of some other specific ion. As an example, enzyme may reduce or oxidize nicotinamide adenine dinucleotide. Under suitable conditions NADH produced or consumed by the enzyme can be followed by the redox sensitive photoresponsive electrode.

Various circuits may be employed for determining the state of the medium adjacent to the surface. Besides the photoresponsive sensing electrode, there will be at least one counterelectrode, or there may be a counterelectrode for each compartment or channel of the device. The same or different counter electrode may serve as a controlling or reference electrode.

Various electrodes of a variety of materials may be used, so long as the materials of the electrode do not adversely affect the photoresponsive electrode, are not adversely affected by, and preferably not sensitive to the electrically communicating medium, and do not adversely affect the electrically communicating medium. Illustrative electrodes include such materials as platinum, gold, stainless-steel, silicon/silicon oxide, rhodium, palladium, aluminum/aluminum oxide, titanium/titanium oxide, silver-silver chloride, calomel, conducting glass electrode ($SnO_2$, $InO_2$ or ITO), etc. In some instances it may be desirable to encase the electrode in an electrically communicating shield, e.g., gelatin.

In one embodiment, there are two electrodes, the working electrode and a controlling/reference electrode. The potential between the sensing electrode and the controlling/reference electrode can be varied by varying the potential applied to the controlling/reference e electrode with respect to the sensing electrode. The light emitting diode or other light source is powered with an external electronic circuit so as to emit light which may vary in intensity with time, in a regular pattern, e.g., square-wave, sine-wave, etc., resulting in a time dependent response of the sensing electrode, which can be detected by measuring the current through the controlling/reference electrode required to maintain a constant potential between the sensing electrode and the controlling/reference electrode.

In this configuration the peak to peak amplitude of the periodically varying current through the controlling/reference electrode varies as a function of the chemical environment at the sensing electrode and as a function of the potential applied between the sensing electrode and the controlling/reference electrode.

Desirably, the conducting medium with which the counterelectrode is in electrical communication, e.g., immersed, will have a small amount of redox couple or electron transfer agent, since in some instances the presence of the agent enhances the stability of the observed signal. Conveniently, the concentration will be in the range of about 1 $\mu$M to 0.1M. Inorganic redox couples may be employed, such as $Fe^{+3}/Fe^{+2}$, $Cu^{+2}/Cu^{+1}$, and $Mn^{+3}/Mn^{+2}$, or the like, where the metal ions may be complexed with such ligands as cyanide, ammonia, halide, etc.

The sample may be subjected to prior treatment, may be used neat, may be extracted, chromatographed, purified, diluted, concentrated, filtered or the like. The sample may be combined with the reagents, the reactions allowed to occur and the resulting medium added to the device for determination. Alternatively, the sample and reagents may be combined in the presence of the device or added to the device after combining but prior to reaction beyond a desired extent. After adding the sample(s) to the device, measurement may then be made by interrogating with photoillumination at each site individually and with each site connected to appropriate electrical circuitry.

The subject devices may be fabricated in a wide variety of ways. For example, where using a monolithic semiconductor, particularly a silicon or other photoresonsive or semiconductor wafer, the electrically conducting layer, particularly the metal layer, may be deposited at a plurality of sites on the surface of the wafer. Desirably, the insulative layer is present on the surface of the water so as to avoid the need for a high resistance in the circuit. Where an insulative layer is not present for a semiconductor material reactive with the medium, an insulation layer will be formed after forming the electrically conductive layer. The semiconductor will be doped at each element site or may be doped uniformly thorughout the monolithic semiconductor.

In general, for sensitive detection of species such as organisms, analytes, catalysts, or enzymes, it is advantageous to concentrate these species into a small volume in contact with the surface of the photoresponsive working electrode. This may be done by various means, e.g., filtration, capture onto a solid phase (as in hetergeneous immunoassays), passive adsorption to a solid phase, or by chemical partitioning into a liquid subphase, to name only a few. Once the species have been concentrated, it is advantageous to exclude extraneous electrolyte from the surface of the photoresponsive working electrode so that the redox compounds, hydrogen ion, or other specific ions generated by the detected species are not diluted, unnecessarily, into a large volume. Various mechanical devices, such as pistions, diaphragms, movable septae, and the like may be used to exclude excess electrolyte volume. For the same purpose it will be advantageous to employ electrolytes with relatively low capacity to buffer changes in redox potential or changes in hydrogen ion or other specifically-detected ion concentrations so that large changes in potential are produced by low rates of chemical reaction.

For detection of species which cause a change in redox potential, it is desirable to restrict the conductive (e.g., metal) layer on the photoresponsive working electrode to contact only the redox species in the confined small volume. In this way, the redox potential in the small volume may change independently of the redox potential of a larger volume which may be in electrical contact with the small volume through a salt bridge.

For detection of pH changes, the buffer capacity of the medium usually will be between 0.01 and 100 mM, more usually between 0.1 and 10 mM. For the detection of redox potential change, the concentrations of oxidizable or reducible species detected by the photoresponsive working electrode generally will be between 1 nM and 10 mM, more usually between 0.001 and 1.0 mM.

For further understanding of the invention the drawings now will be considered.

In FIG. 1 is depicted a diagrammatic cross-sectional (side) view of a device (10) having a porous reagent pad (12) having a plurality of redox-measuring sites (14). The device has a monolithic semiconductor (16) coated with insulative layer (18). A plurality of electrically-conducting layers (20) are coated onto insulative layer (18). The semiconductor (16) is connected at ohmic contact (22) to lead (24) which is connected to a circuit which is not shown. Sealingly mounted on semiconductor (16) is O-ring (26) which provides for a liquid seal with the device body (28) and semiconductor insulative layer (18). The device body (28) and O-ring (26) are cut away at the top of the device to allow for introduction of the fluid medium (30) and the porous reagent pad (12). The device body (28) serves to retain the semiconductor (16), the fluid medium (30) and a moveable piston (32). The moveable piston serves to minimize the volume adjacent to each of the sensing electrically-conducting layers (20) so as to provide for sensitive detection of redox reactions at these redox measurement sites (14). The moveable nature of the piston allows for introduction and removal of the porous reagent pad (12). The fluid medium is prevented from leaking around the piston by O-ring seals (31). The fluid medium is maintained in contact with the regions of the insulative layer including those which are coated with the electrically conducting layer, e.g. a metal layer, for the redox potential measurement. The fluid medium is buffered to provide for a substantially constant pH so that changes in pH during redox measurements will be negligible. The fluid medium also contains the redox pair which provides for the initial redox potential, the subsequent change of which is related to the amount of analyte in a sample.

A common reference electrode (34) may be provided, such as silver-silver chloride, calomel, or the like, which electrode is connected to the common circuit and to the fluid medium (30) through lead (36). Similarly, a common controlling electrode (38) is provided which contacts the fluid medium (30) through lead (40).

When the moveable pistion (32) presses against the porous reagent pad (12), electrical continuity is maintained to each of the redox measurement sites (14) through the buffered medium contained in the porous reagent pad (12). In effect, the porous reagent pad becomes a conducting salt bridge.

In order to stimulate the photoresponse, illuminated regions (42) of the semiconductor (16) are illuminated with oscillating intensity light from light emitting diodes (LEDs) (44). The LEDs are connected to LED-driving circuitry which is not shown. The illuminated regions (42) are selected to be opposed directly across from corresponding conductive layers at the surface of the insulator (18). More precisely, the potential of the conductive layers affects the electric field in surface regions (46) of the semiconductor which are opposed directly across the insulative layer (18) from the respective conductive layers. Photogenerated charge carriers must diffuse into the respective surface regions (46) of the semiconductor (16) in order to produce a photocurrent which is modified by the potential of the respective conductive layers (20). Thus, the semiconductor (16) must not be so thick that photogenerated charge carriers cannot diffuse from the illuminated regions (42) to the surface regions (46) during the lifetime of photogenerated minority carriers. Typically, this distance is 3 mm or less, in pure silicon, for example. This minority carrier diffusion distance similarly limits the closeness of spacing between independent surface sensing regions (46). This minority carrier diffusion distance may be decreased by creating recombination sites in the semiconductor, for example in silicon by introduction of gold impurities into the silicon crystal (Bullis, "Properties of Gold in Silicon," *Solid State Electronics* (1966) 9:143). In this case, the semiconductor (16) correspondingly must be thinner.

In FIG. 2 is depicted a plan view of the device (10) looking first at the moveable piston (32), the device body (28), and leads (36) and (40) to the reference and controlling electrodes, respectively. Protruding from a hole in the top of the device body (28) is the porous reagent pad (12). Hidden from direct view (indicated by the broken lines) is the portion of the porous reagent pad (12) that is inserted into the device body. Similarly hidden from direct view and indicated by broken lines are the redox measuring sites (14) (outer circles), the electrically-conducting layers (20), and the LEDs (44) (inner circles). Coated onto insulative layer (18) are the plurality of electrically conducting layers (20).

In carrying out an assay, such as a solid-phase, indirect, enzyme-linked, immunosorbent assay (ELISA); the reagent pad is used as the solid-phase immunosorbent material. Depending on the presence of an analyte, more or less enzyme capable of changing the redox potential is bound to redox measuring sites (14) on the porous reagent pad (12). The pad (12) is inserted into the device (10) while the moveable piston (32) is in the withdrawn position. The moveable piston then is employed to expel excess fluid medium (30) from the volume adjacent to the redox measuring sites (14) within the reagent pad (12). The rate of redox potential change at each of the redox measuring sites (14) then is measured employing the LEDs (44) for illumination, and the electrode and attached circuitry (not shown) for applying a bias potential and for measuring the light-induced photocurrent (as noted previously). The rate of redox potential change at each site (14) thus determined is related to the concentration of analyte in the sample previously introduced to individual redox measuring sites (14) by way of a similarly run assay procedure incorporating an analyte standard. The standard assay procedure may be run before, after, or at the same time as the assay procedure. When run at the same time as the assay procedure, standard assay procedure may be carried out at redox measuring sites (14) different from those where unknown analyte concentrations are determined. Alternatively, standards and unknowns may be determined separately in different devices (10).

In making the determination, each of the illuminating sources (44) may be activated so as to interrogate a particular redox measuring site (14) and provide an electrical signal determined by the circuit. Although the device shown in FIG. 1 has only a single ohmic contact (22), redox measurements may be performed at a multiplicity of redox measuring sites (14) by activating sequentially in a known-order, the LEDs (44). At any one time only one of the LEDs is activated. In turn, each of the LEDs may be activated and the bias potential applied to the controlling electrode adjusted so as to maintain a predetermined photosignal. The potential of the reference electrode (34) is measured by circuitry (not shown) and, in this mode of operation will be affected by the redox potential of the fluid medium (30) at a redox-measuring site (14) adjacent to an electrically (conductive layer 20). The electrically conductive layer is on the opposite side of the insulating layer (18) from a surface region (46) of the semiconductor. The surface region is within minority carrier diffusion distance of the illuminated region (42) of the semiconductor which in turn is illuminated by a selected LED (44). Alternatively, the redox potential may be measured by activating, in turn, each LED in known sequence but instead of maintaining a fixed photoresponsive signal, the bias potential applied to the controlling electrode is varied with time so as to ramp the potential through the region where zero electric field is produced in the semiconductor surface region (46) that is associated with the activated LED (44). In this way, with a redox potential standard incorporated at the redox measuring site (14), a characteristic relationship of photoresponsive versus reference electrode potential is generated and stored into electronic memory by a circuit (not shown). A change is redox potential at the relevant redox measuring site (14) away from the standard reference electrode will cause the characteristic relationship to change.

This measured deviation in the relationship between the photoresponse and reference electrode potential, upon either a change in the porous reagent pad (12) or upon passage of time, may be recorded and then related directly to the change, or rate of changes, or the redox potential at the relevant redox-measuring site (14). One method of examining the deviation so generated is to calculate the second derivative of the photorespose versus reference electrode potential and then determine where the second derivative a zero, crossing between large positive and negative values. A shift with time in the reference electrode potential giving the second-derivative "zero crossing," may be measured and related directly to the rate of change in redox potential at the respective redox-measuring site (14).

In FIG. 3 is depicted an individual flow cell device (50). The flow cell device has working electrode (52) which is comprised of the semiconductor layer (54), the insulative layer (56) and the electrically conductive layer, e.g., metal layer (58). The working electrode (52) is connected to an external circuit by ohmic contact (60) and lead (62). Mounted on the working electrode (52) is O-ring (64) in sealing engagement with the working electrode (52) and container cylinder (66). Conduit (68) leads into the container (66) for continuously introducing a sample stream of electrolyte (69). Conduit (70) serves as the outlet for removing the sample stream from container (66). Reference electrode (72) and controlling electrode (74) are provided for connection to the circuit, not shown. An illuminating source (76) is provided, which illuminates both the area (78) underneath the metal coating and the area (80) where the insulative layer (56) is uncoated and in direct contact with the sample medium.

The semiconductor layer (54) forms a Schottkey barrier junction where it contacts the conductive metal layer (58). The characteristics of such junctions are well known (see for example, Sze, S. M., Physics of Semiconductor Devices). When the lead (62) of the semiconductor (54) is biased via the controlling electrode (74) by circuitry (not shown) so as to cause depletion of majority charge carriers from the semiconductor junction region (82) adjacent to the conductive metal region (58), current is inhibited from passing through the junction region (82), except when the semiconductor is illuminated in the area under the metal coating (78), so as to produce minority charge carriers within the junction region (82). Thus, the LED (76) may be used to switch the junction region (82) from the nonconducting to the conducting state.

In operation, a chemical reaction involving oxidation or reduction (i.e., a redox reaction) may be monitored as demonstrated by the following example: The semiconductor (54) is chosen to be p-type for example, boron doped silicon for detection of a reducible substance, such as oxygen, which may be present at the surface metal layer (58) in the sample electrolyte (69). Where the p-type semiconductor is negatively biased with respect to the reference electrode (72) so that majority charge carriers are depleted from junction region (82), and when LED (76) is not activated so that the semiconductor is maintained in the dark condition, direct current is inhibited from flowing through a series circuit involving the semiconductor layer (54), the metal layer (58), the electrolyte (69), and the controlling electrode (74), even when the reducible species such as oxygen, is present in the electrolyte (69). This is so because junction region (82) is in the nonconducting state. Activation of LED (76), however, switches the junction region (82) into the conducting state and direct current or charge flows in the circuit as determined by the quantity of reducible species, i.e., oxygen, at the surface of the metal layer (58) in the sample electrolyte (69). The amount of oxygen present may be determined from the current time relationship (after activation of the LED) and the constants of the system by the well known Cottrell equation (D. T. Sawyer, and J. L. Roberts, Jr., Experimental Electrochemistry of Chemists, John Wiley & Sons 1974). Alternatively, an oxygen standard may be provided to calibrate the system. The LED (76) may be activated in a periodic fashion so as to determine the rate of oxygen depletion due to an ongoing chemical reaction in the sample electrolyte. For example, an enzyme-linked immunoassay may be performed by monitoring the rate of oxygen depletion due to an enzymatic reaction, such s the oxidation of glucose by oxygen that is catalyzed by the enzyme glucose oxidase. In such an immunoassay, conjugates of the enzyme with one member of a binding pair, such as an antigen- or hapten-specific antibody are first prepared and subsequently used to detect either the opposite members of the binding pair, i.e., antigen or hapten, or other specific antibody molecules (by way of competitive binding). A large number of variations of methods of performing such immunoassays are well known to those skilled in the art of performing immunoassays. The only requirement for the detection by the presently disclosed photosensitive redox device is that the enzyme and enzyme substrate is chosen so that either the enzyme substrate(s) or enzyme products are oxidized or reduced readily by the metal conductive layer (58) when the junction (82) is switched into the conducting mode by LED (76). For detection of oxidizable species rather than reducible species, preferably the semiconductor will be n-type, such as phosphorous-doped silicon, and the semiconductor will be positively biased with respect to the reference electrode (72) so that again, majority charge carriers are depleted from the junction region (82). As in the previous case, when LED (76) is activated so as to illuminate semiconductor region (78) under the metal layer (58), the junction region (82) becomes conducting so as to produce a direct current in the series circuit, as in the above example for detection of reducible species. In this case, for detection of oxidizable species, however, the flow the direct current will be in the opposite direction and, thus, of opposite sign. As in the previous case for detection of reducible species, the magnitude of direct current or the current-time relationship may be measured as a means of quantitating the amount of oxidizing species present in the sample electrolyte (69) at the surface of the conductive layer (58).

The device shown in FIG. 3 may be constructed so as to have a multiplicity of separate conductive regions (58) in contact with a sample electrolyte which may have different redox potentials at the surface of the different conductive regions. Such special differences in redox potential may be created by introduction of different electrolyte compositions at the surface of the respective conductive regions, or alternatively the different redox potentials may be generated with time by varying the rate of a chemical reaction occurring at the respective conducting regions. The chemical reaction may be catalyzed by an enzyme, for example, and the amount of enzyme or other catalyst present, could be measured by monitoring the rate of current or potential change at each one of the conductive regions (58). In the case where multiple conductive regions are present on a single semiconductor substrate (54), multiple LEDs (76) or other light sources also will be present. As in the previous case shown in FIGS. 1 and 2, the LED or other light source which is activated determines the region of the sample electrolyte where the redox reaction is measured.

Additionally, rather than sequentially enabling the LEDLs, alternating currents of different frequencies could be applied to the different LEDs, with each compartment being identified by a different frequency.

Various types of circuits may be employed for determination of the photoresponsiveness of the semiconductor devices shown in FIGS. 1, 2, and 3 as a function of analyte concentration. One particular circuit which may be employed allows for operation in either one of two modes. In one mode, the potential between the controlling or reference electrode and the sensing electrode is maintained constant and the amplitude of the sinusoidal, either alternating or direct (faradaic), current through the sensing electrode in response to sinusoidal illumination of the sensing electrode is used as a monitor of the environment of the sensing electrode at the site of illumination. This is referred to as the CP mode. In a second mode, the circuit automatically varies the potential between the controlling or reference electrode and the sensing electrodes so as to maintain a constant amplitude sinusoidal current through the sensing electrode during illuminating with constant modulation of light intensity. In this configuration, the potential between the controlling or reference electrode and the sensing electrode is used as a monitor of the sensing electrode at the site of illumination. This is referred to as the CAM mode.

Figure 4:
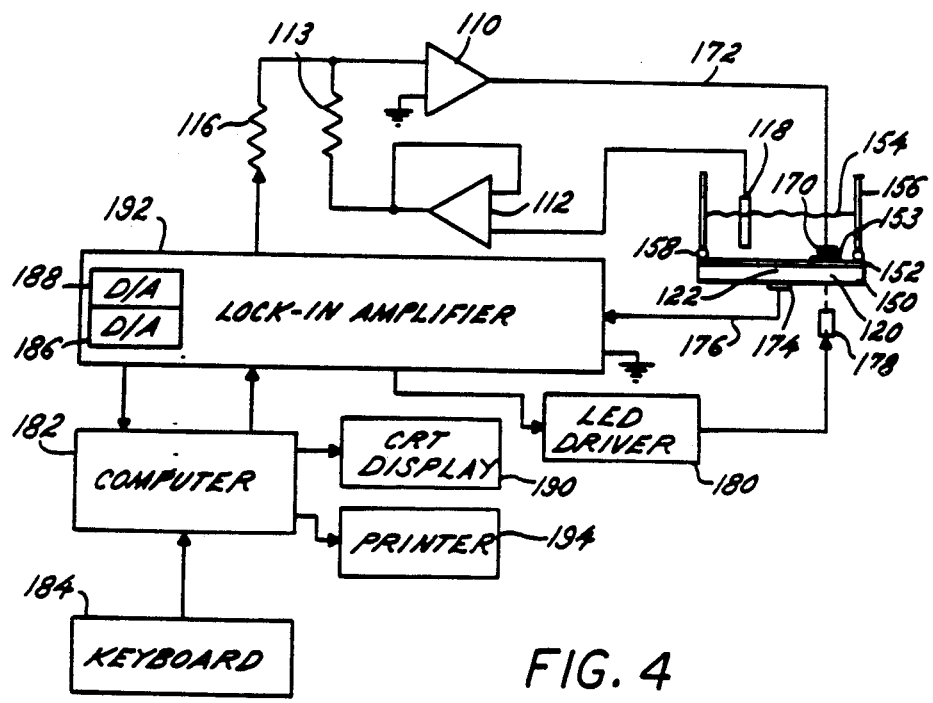
FIG. 4 is an exemplary circuit for use with the device.

Shown in FIG. 4 is a schematic diagram of a computer-controlled apparatus which may be used to produce and measure a photocurrent in accordance with the present invention. A semiconductor wafer 150 is covered with an insulator 152, on which is electronically conductive layer 153, which insulator and conductive layer are in contact with an electrolyte 154 enclosed by a chamber wall 156 sealed to the insulator suface by a rubber gasket 158. Operational amplifiers 110 and 112, together with resistors 113 and 116, reference electrode 118, and a voltage signal from a lock-in amplifier 192 via operational amplifier 110, lead 172 and controlling electrode 170 function to determine the potential of the electrolyte 154 with respect to the bulk of the semiconductor 150. The potential of the semiconductor bulk is connected to virtual ground by an ohmic contact 174 attached to the underside of the semiconductor wafer 150 and to a copper lead 176 connected to the current input terminal of the lock-in amplifier 192 (Model SR530, Stanford Research Systems, Palo Alto, Calif.). The ohmic contact 174 is made by evaporating approximately 0.5 micron of gold-1% arsenic onto the (bare) etched back surface of a silicon wafer, etching away the gold from regions where light penetration is desired and then alloying the gold into the silicon at 450° C.

The semiconductor 150 is a 4-inch diameter wafer of N <100> silicon of approximately 10 to 15 ohm-cm resistivity. The insulator is composed of approximately 340 angstroms of silicon oxide adjacent to the silicon and overlaid with 1000 angstroms of silicon nitride deposited by chemical vapor deposition from a reaction of dichlorosilane and ammonia at about 800° C. in a low pressure chamber. The wafers are subsequently annealed in a hydrogen ambient at 1050° C. for 1 hour. The metal layer(s) 153 consists of a one-half inch circle of approximately 5000 angstroms of chromium followed by 5000 angstroms of gold, each deposited by evaporation in a low pressure chamber.

Semiconductor regions 120 and 122 are the, so-called, space charge regions of the semiconductor-insulator interface. Semiconductor region 120 is that portion of the space-charge region which is adjacent to that portion of insulating layer 152 which, on the opposite side, is adjacent to electronically conductive layer 153. In contrast, semiconductor region 122 is that portion of the space-charge region which is adjacent to the portion of the insulating layer 152 which, on the opposite side, has no electronically conductive layer.

A light-emitting diode (LED) 178 is powered by a LED driver 180 so as to irradiate the semiconductor 150 with light of sinusoidally modulated intensity. In order to monitor redox potential, the semiconductor 150 is irradiated, customarily from the side opposite the electrolyte medium 154, so as to provide photogenerated minority charge carriers within semiconductor region 120 (i.e., the light beam is directed directly under the electronically conductive layer). The frequency of modulation is controlled by an oscillator circuit within the lock-in amplifier 192 which, in turn, is controlled by a computer 182 having a keyboard 184. Analog data is converted into digital form by an A/D converter 186 within the lock-in amplifier 192. Similarly, a D/A converter 188 converts digital instructions from the computer 182 into analog form which, in turn, control various lock-in amplifier settings and the potential of the electrolyte 154 with respect to the semiconductor 150. Experimentally acquired data may be viewed on a CRT display 190 and permanently copied by a printer 194. An advantage of the lock-in amplifier 192 is that it may be set to reject unwanted electrical signals (noise), thus improving greatly the signal-to-noise ratio for very small signals.

A number of studies were carried out. Unless otherwise indicated, the measurements were carried out at room temperature and the electrolyte is an aqueous solution of 0.15M NaCl and 0.02M sodium phosphate, pH 7.0, with 10 mM potassium ferricyanide and 10 mM potassium ferrocyanide as the redox couple. The LED emits at a peak wavelength of 880 nanometers (Radio Shack XC-880-A) and irradiates approximately 0.28 $cm^2$ of the semiconductor surface opposite the insulator under the electronically conductive (gold) layer 153. Unless otherwise indicated, the LED intensity is sinusoidally modulated 100% at 10 kHz. The controlling electrode is a strip of platinum of about 0.2 $cm^2$ surface area, and the reference electrode is either Ag/AgCl with 3MKCl or alternatively a saturated calomel electrode (SCE).

The alternating photocurrent produced by the intensity-modulated irradiation of the semiconductor is measured by a lock-in amplifier 192 (Model SR530, Stanford Research Systems, Palo Alto, Calif.). The potential of the electrolyte 154 with respect to the semiconductor 150 is programmed to vary, i.e., ramped digitally, at approximately 50–300 millivolts per second in steps of 5–50 millivolts per step starting at about 200–2000 millivolts on the accumulation side of the flat-band voltage and ending at about 200–2000 millivolts on the depletion side of the flat-band voltage. (The flat-band voltage is the applied potential necessary to produce zero, or minimum mean, electric field in the region of the semiconductor adjacent to the insulator. Accumulation conditions exist when the electric field is such that majority charge carriers accumulate in this region of the semiconductor, and depletion conditions exist when the electric field is such that majority charge carriers are depleted from this region.)

The amplitude of the alternating photocurrent is low when the semiconductor is biased into accumulation and approaches a maximum when the semiconductor is biased increasingly into depletion. The tracking bandpass filter of the lock-in amplifier is set to reject current signals which appear at frequencies other than 10 kHz. Additionally, the lock-in amplifier can be set to reject current signals that are out of phase with the photocurrent signal. To accomplish this, first the phase of the photocurrent signal is measured by the lock-in amplifier when the semiconductor is biased into the depletion region, where the alternating photocurrent signal is maximum. This measured phases then selected for phase discrimination by the phase-sensitive detector within the lock-in amplifier. Subsequently, only this "in phase" component of the photocurrent is analyzed.

An example of the data obtained with the use of both the bandpass filter and the phase-sensitive detector is shown in FIG. 5 and the second derivative of this data is shown in FIG. 6. The amplitude of the modulated LED flux was adjusted by regulating the LED current modulation so that the maximum alternating photocurrent obtained was approximately 0.5 microamp (RMS). As can be seen from FIG. 5, the amplitude of the alternating photocurrent is relatively low when a positive bias potential is applied to the reference electrode, which biases the n-type semiconductor into accumulation. As a more negative bias potential is applied, passing through the flat-band potential, the amplitude of the alternating photocurrent increases, approaching a maximum value at increasingly negative bias potentials where the n-type semiconductor is biased into depletion. The result is a characteristic, sigmoidally shaped curve.

Figure 7:
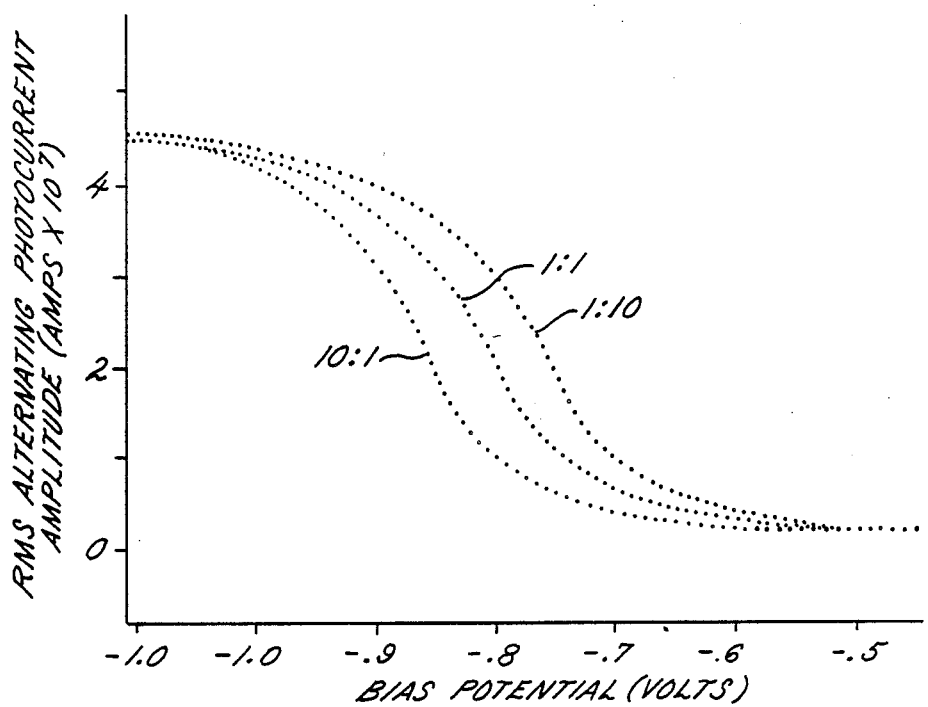
FIG. 7 is a graph of the effect of the alternating photocurrent amplitude as a function of bias potential when the redox potential of the electrolyte is altered by changing the ratio of ferricyanide to ferrocyanide anion concentration.

The sharpness of the response, or more precisely, the change in applied bias potential necessary to cause a transition from a low measured photocurrent to a high measured photocurrent, appears to be indicative of the uniformity of the electric field within the semiconductor space charge region. The more uniform the electric field, the sharper the transition will be. FIG. 7 shows the effect on the photoresponse versus bias voltage response when the redox potential of the electrolyte is altered by changing the ratio of ferricyanide to ferrocyanide anion concentration in aqueous electrolyte 154.

Figure 8:
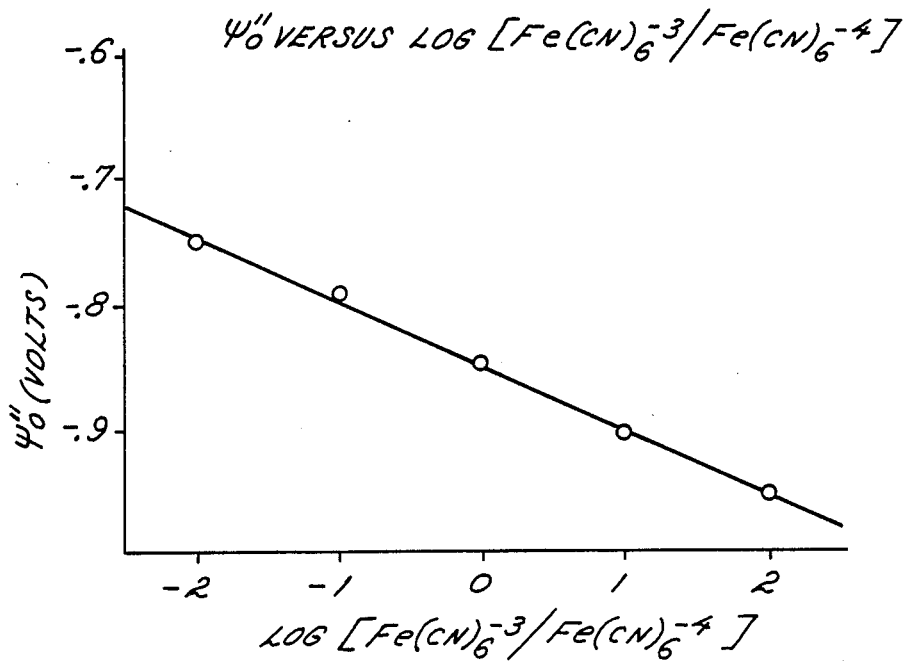
FIG. 8 shows the change in $\Psi_O''$ as a function of the logarithm of the [ferricyanide]/[ferrocyanide] ratio.

Decreasing the ratio of ferricyanide/ferrocyanide causes the photocurrent versus bias potential relationship to shift along the bias potential axis in the positive direction. A more negative redox potential created upon decreasing this ratio causes metal layer 153 to acquire negative charge. Therefore, in order to maintain a constant electrical field within region 120 of the semiconductor, the potential of electrolyte 154, as monitored by reference electrode 118, must be biased in the positive direction by operational amplifier (110) via controlling electrode (170). The apparent shift in bias potential caused by changes in redox potential of the electrolyte may be quantitated conveniently by measuring the potential ($\Psi_o''$) where the second derivative of the photocurrent versus bias potential response crosses zero between a maximum and a minimum (see for example, FIG. 6). FIG. 8 shows the change in $\Psi_o''$ as a function of the logarithm of the [ferricyanide]/[ferrocyanide] ratio. The observed change in $\Psi_o''$ is about 59 millivolts per ten-fold change in [ferricyande]/[ferrocyanide] ratio. This response is near the theoretical response obtained from the Nernst equation for a redox reaction with a one-electron change observed at room temperature (23° C.).

Figure 9:
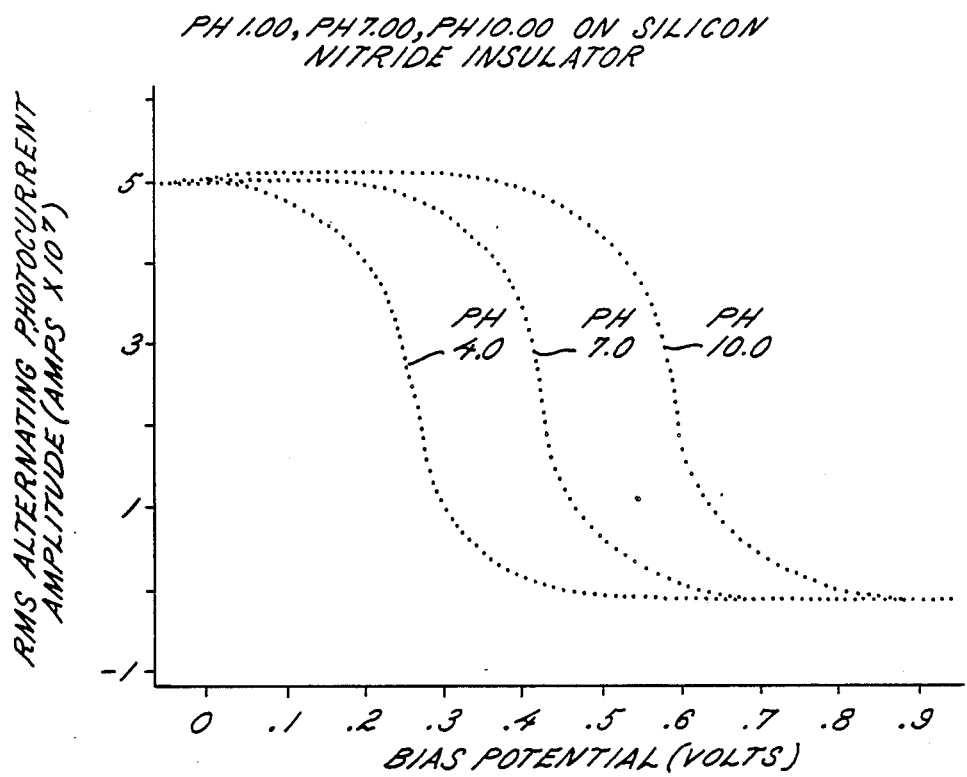
FIG. 9 is a graph of the alternating photocurrent amplitude as a function of the bais potential for electrolytes at pH 4, 7, and 10.
Figure 10:
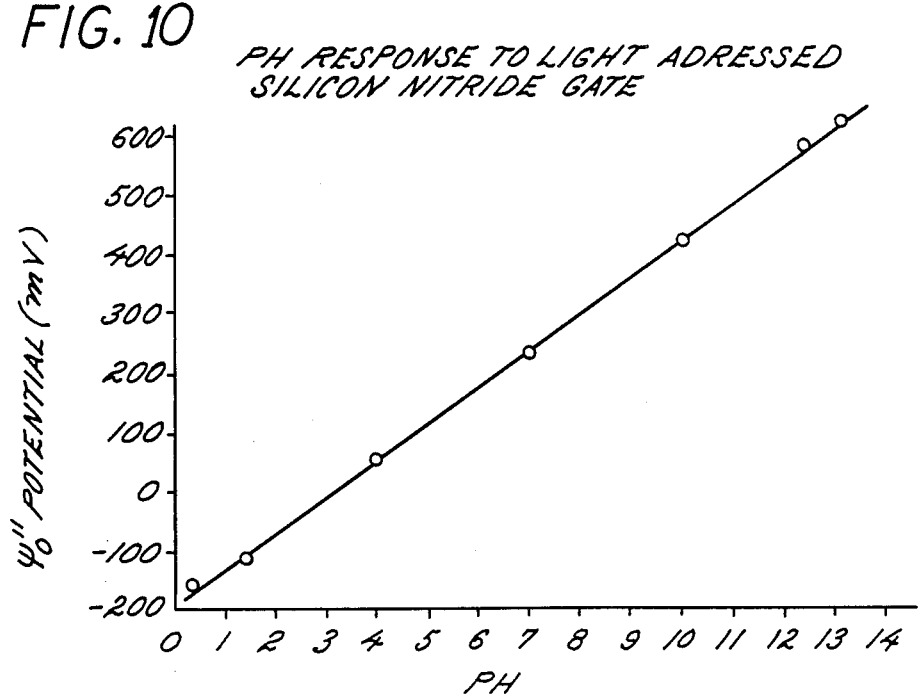
FIG. 10 is a graph of the change in $\Psi_o'$ as a function of pH.

The pH of the electrolyte medium 154 also may be monitored with the device and circuitry shown in FIG. 4. To measure pH, the insulating layer 152 is a pH responsive material, such as silicon dioxide, silicon nitride, aluminum oxide, titanium dioxide, tantalum dioxide, or the like. For measurement of pH, the semiconductor 150 is irradiated so as to produce minority charge carriers within semiconductor region 122. All other conditions including semiconductor, insulator, irradiation, and bias conditions are as indicated previously for measurement of redox potential. Shown in FIG. 9 is the alternating photocurrent amplitude as a function of bias potential, as measured by reference electrode 118, for electrolytes with pH 4.0, 7.0, and 10.0 (Fisher pH standards SO-B-101, SO-B-107, and SO-B-115 respectively). Increasing pH causes the photocurrent versus bias potential relationship to shift along the bias potential axis in the positive direction. Decreasing the hydrogen ion concetration in the electrolyte (e.g., by changing pH from 4.0 to 7.0) causes hydrogen ions to dissociate from the insulator surface leaving the surface more negatively charged relatively to the starting condition. Therefore, in order to maintain a constant electrical field within the semiconductor region 122, the potential of electrolyte 154 as measured by reference electrode 118 must be biased in the positive direction by operational amplifier 110 via controlling electrode 170. As for the case where redox potential was quantitated, the apparent shift in bias potential caused by changes in pH of the electrolyte may be quantitated conveniently by measuring the potential $\Psi_o''$ where the second derivative of the photocurrent versus bias potential response crosses zero between a maximum and a minimum (see for example, FIG. 6). FIG. 10 shows the change in $\Psi_o''$ as a function of electrolyte pH. The observed changes in $\Psi_o''$ is about 59 millivolts per pH unit, again near the theoretical response obtained from the Nernst equation for a unity charge transfer reaction at 23° C.

A single light source, conveniently an LED, may be employed to measure specific ion concentrations, such as pH and redox potential. For the measurement of both pH and redox potential, the following example is given:

The insulating layer 152 (see FIG. 4) is made of a pH-responsive material. The electronically conductive layer 153 is made to be about one-half the area of illumination provided by the LED 178. Under these conditions, the device shown in FIG. 4 may be employed to measure both the pH and redox potential of medium 154 relative to either pH or redox potential standards. An LED 178 is employed to illuminate semiconductor 150 so that photogenerated minority charge carriers reach both regions 120 and 122 of the semiconductor space-charge region adjacent to the insulator. Semiconductor region 120 is adjacent to that part of insulative layer 152 which is covered by electronically conducting layer 153. Semiconductor region 122, in contrast, is adjacent to some portion of that part of insulative layer 152 which is not covered by electronically conductive layer 153. The LED 178 (Radio Shack XC-880-A) emits peak intensity at a wavelength of 880 nm and irradiates approximately 0.28cm$^2$ of the semiconductor surface opposite to the electrolyte medium 154. The LED intensity is modulated 100% at 10 kHz by LED driver 180 which is controlled by an oscillator and lock-in amplifier 192 which in turn is controlled by computer 182 through keyboard 184.

Semiconductor substrate 150, insulating layer 152, and electronically conducting layer 153, are as described previously except that the chromium-gold conducting layer was etched to a 4.2 mm diameter spot after first masking the spot in with Scotch® magic transparent tape (3M) The etching solution to remove the gold layer is composed of 400 g potassium iodide, 100 g iodine, and 1600 g water. After removing the unmasked gold surface layer, the remaining chromium adhesion layer is removed by etching in a solution of 20 g potassium ferricyanide, 10 g sodium hydroxide, and 100 g water. The tape mask is removed with acetone. The controlling electrode is a strip of platinum about 0.2 cm$^2$ surface area. The alternating photocurrent produced by the intensity-modulated irradiation by LED is measured by lock-in amplifier 192 (Model SR530, Stanford Research Systems, Palo Alto, CA.), as described previously. The measured analog value is converted to a digital signal by analog-to-digital converter (A/D) 186 within lock-in amplifier 192 and is sent to computer 182 and the results are observed on CRT display 190 and imprinted onto paper by printer 194.

The data shown in FIG. 11 were generated with the device and circuitry thus described with an aqueous solution of 100 mM sodium phosphate, 2.5 mM potassium ferricyanide, 2.5 mM potassium ferrocyanide, pH 7.2 as the electrolyte medium 154. A uniformly distributed light flux from LED 178 was employed to illuminate approximately equal areas of semiconductor regions 120 and 122. Beginning at the right of FIG. 11 where the bias voltage is such that majority charge carriers are accumulated in semiconductor regions 120 and 122, the amplitude of the alternating photocurrent produced by the device is very small. There is, however, an initial step increase in the amplitude when a substantial fraction of either semiconductor region 120 or semiconductor region 122 is biased so as to cause depletion of majority charge carriers. For the n-type semiconductor employed, this condition occurs when the controlling electrode potential is made more negative with respect to the semiconductor (which is maintained at virtual ground). A second step increase in alternating photocurrent is observed when a second substantial fraction of semiconductor region 120 or 122 is biased into depletion. Separate experiments employing a narrow beam of light to provide photo-generated minority charge carriers separately in either semiconductor region 120 or semiconductor region 122 showed that the initial step increase in the amplitude was due to excitation of semiconductor region 122 (under the pH responsive insulator surface) and the second step increase in the amplitude was due to excitation of semiconductor region 120 (under the redox-potential-responsive, electronically conductive layer 153).

The data shown in FIG. 11 were generated with the areas of semiconductor regions 120 and 122 (that were effectively excited by minority charge carriers produced by uniform light flux from LED 178) approximately equal. Thus, the amplitude of the first and said second steps shown in FIG. 11 were approximately equal. In FIG. 12 is shown the first derivative of the data shown in FIG. 11. There are two clear minima in the first derivative. One minimum is near −0.08 volts and corresponds to the initial step increase in alternating photocurrent shown in FIG. 11. The second minimum shown in FIG. 12 is near −0.90 volts and corresponds to the second step increase in alternating photocurrent shown in FIG. 11. The exact voltage position of the first minimum is dependent upon the pH of electrolyte 154. The voltage response of the first minimum to changes in pH (data not shown) is similar to the pH-dependent voltage response shown in FIGS. 9 and 10 with about 0.059 volts negative shift on the bias potential axis for every 10-fold increase in hydrogen ion concentration (i.e., for a 1 pH unit change). The voltage response of the second minimum is dependent upon the redox potential of electrolyte 154. The voltage response of the second minimum to changes in redox potential (data not shown) is similar to the redox-potential-dependent voltage response shown in FIGS. 7 and 8, again with about 0.059 volts negative shift on the bias potential axis for every 10-fold increase in the ratio of ferricyanide to ferrocyanide.

Figure 13:
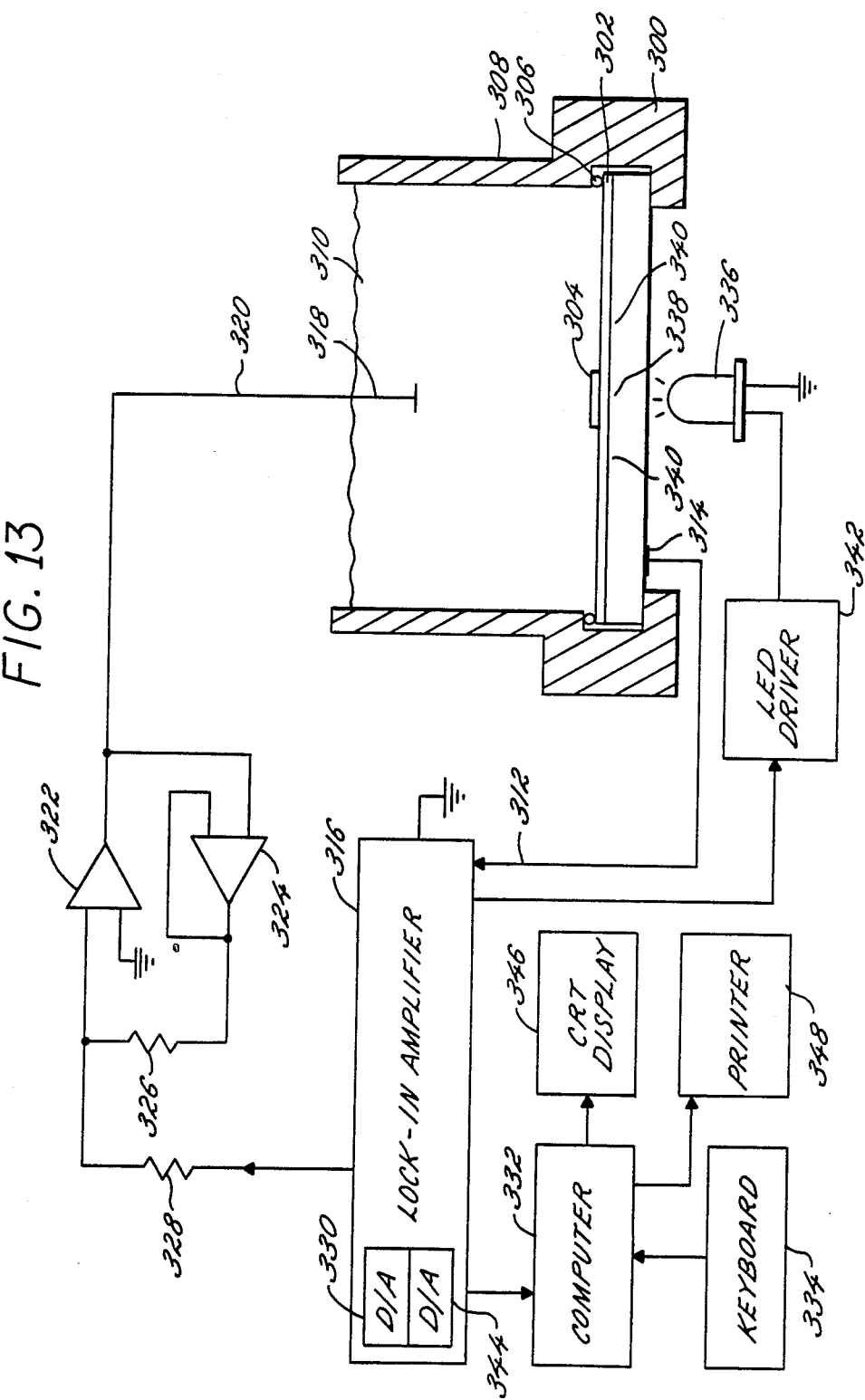
FIG. 13 is an alternative circuit shown with a diagrammatic view of a device which permits redox potential measurement without a separate reference electrode.

Shown in FIG. 13 is a particularly convenient embodiment of the present invention.

The device is useful for measurement of either redox potential or specific ion concentrations, including pH, without employing a separate reference electrode. The basic device and controlling circuitry are shown in FIG. 13. A semiconductor substrate 300 is coated with an insulating layer 302. The insulating layer, in turn, is covered partially by electronically conducting layer 302. An O-ring 306 provides a seal in contact with insulating layer 302 which O-ring is held in place by structure 308. This structure serves both as a chamber wall and a clamping device. Structure 308 thus contains electrolyte medium 310 in which an analyte may be present. Lead 312 electrically connects semiconductor substrate 300 via ohmic contact 314, to the current measurement input of lock-in amplifier 316, which is maintained at virtual ground. Controlling electrode 318 is connected via lead 320 to both the output of operational amplifier 322 and the positive input of operational amplifier 324. The potential of controlling electrode 318 is determined by operational amplifiers 322 and 324, the values of resistors 326 and 328, and the output of a digital-to-analog converter (D/A) 330 within lock-in amplifier 316, which in turn is controlled by computer 322 from keyboard 334.

The above system may be utilized to measure either pH or redox potential, one relative to the other, without the need of a reference electrode. The measurement procedure without a reference electrode is essentially identical to that outlined above, where a reference electrode is employed. The results of A.C. photocurrent versus bias potential measurement (not shown) and the first derivative plot (not shown) are similar to the measurements made with a reference electrode, the results which are shown in FIGS. 11 and 12 respectively. With no reference electrode, however, the exact positions of the first and second step increases in A.C. photocurrent on the bias potential axis are not uniquely dependent upon either pH or redox potential. Similarly, the bias voltage positions of the minima in the first derivatives of this response are not uniquely dependent upon either pH or redox potential. The voltage difference between the first and second step increases in AC photocurrent (or the voltage difference between the minima), however, are constant for a system where both pH and redox potential are held constant. Similarly, this voltage difference may be related to either a single pH value or to a single redox potential (in a unique way) (either pH or redox potential or electrolyte 154) when one parameter is fixed, while the remaining parameter is allowed to vary. In effect, one of the measured AC photocurrent versus bias potential responses become the reference response. Thus, a separate reference electrode is not required for quantitation of changes in the remaining parameter.

Measurements of redox potential at fixed pH and of pH at fixed redox potential were carried out as described above for measurement of either pH or redox potential with a reference electrode, except that the circuit configuration without a reference electrode (shown in FIG. 13) was employed. Shown in FIG. 14 is the difference in bias potential between the two minima in the first derivative of the photocurrent versus bias potential response observed in an experiment where the pH was kept constant at pH 7.0 and the redox potential was varied. The buffer was 0.05M potassium phosphate (Fisher standard buffer Cat. No. SO-B-107). The redox potential was varied by varying the ratio of potassium ferricyanide to potassium ferrocyanide. The redox species present in highest concentration was in all cases present at 1.0 mM. As can be seen from FIG. 14, the bias potential difference between minima (calculated from the bias potential at which the second derivative is zero) is linearly dependent upon the logarithms of the ratio of ferricyanide to ferrocyanide concentrations present in electrolyte medium 310. The response of the bias potential difference to changes in redox potential is similar to the redox potential voltage response shown in FIGS. 7 and 8, with about 0.059 volts of increasing difference for each 10-fold increase in the ratio of ferricyanide to ferrocyanide.

The reciprocal experiment to the one described above was carried out for the determination of pH without a separate reference electrode. Shown in FIG. 15 is the difference in bias potential between the two minima in the first derivative of the photocurrent versus bias potential response observed when the redox potential was kept constant and the pH was varied. The buffer was either 0.05 M potassium biphthalate, pH 4.36 (Fisher, SO-B-101) or 0.05 M sodium-potassium phosphate pH 6.98 (Fisher, SO-B-107) in each case with 10 mM potassium ferricyanide and 10 mM potassium ferricyanide. The pH in each was determined with a standard glass electrode (Fisher Cat. No. 13-639-252). As can be seen from FIG. 15, the bias potential difference between the first derivative minima is dependent upon pH. The voltage response was about 0.055 volts of increasing difference for an increase of one pH unit. The relationship between pH and the difference is simple provided that the redox potential is pH-insensitive. This is approximately true with the redox couple employed (ferricyanide/ferrocyanide) in the range of pH 4.5 to pH 9.5.

Figure 16:
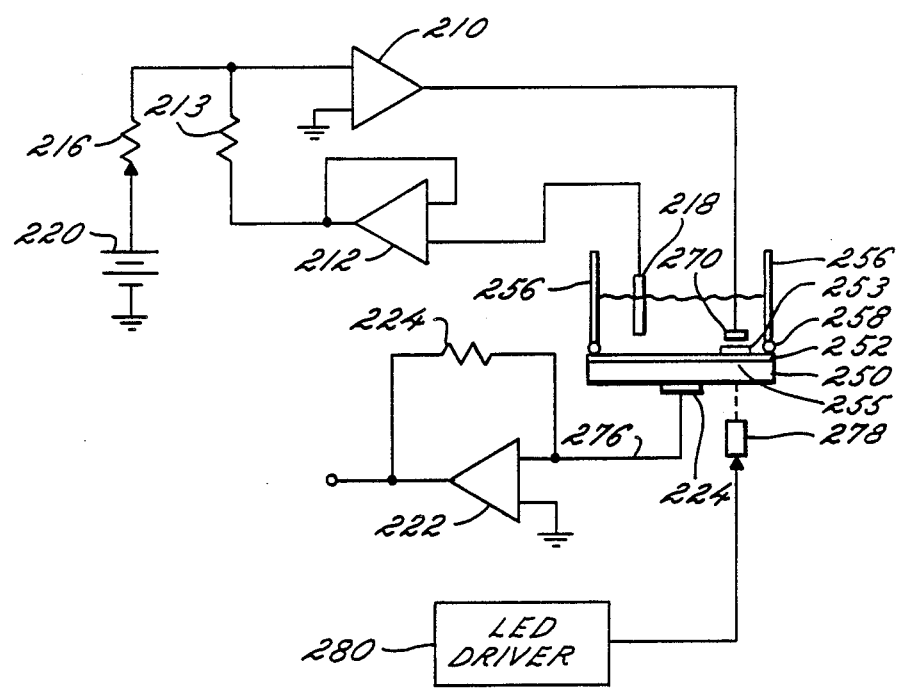
FIG. 16 is a circuit and a diagrammatic view of a device for use in photoresponsive amperometric determinations.

In FIG. 16 a device is depicited for use in amperometric determinations. A semiconductor substrate 250 having both an insulating layer 252 and a conducting layer 253 is brought into physical contact with electrolyte medium (254) containing an analyte of interest. In this amperometric device, electronically conducting layer 253 traverses a perforation in insulating layer 252, so as to make contact with semiconductor substrate 250. Electronically conducting layer 253, preferably, is an inert metal, particularly a noble metal, e.g., gold, platinum, iridium, or the like. Electrolyte medium 254 is retained in contact with insulating layer 252 and electronically conducting layer 253 by means of chamber walls 256, insulating layer 252, and sealing gasket 258. Operational amplifier 210 acts to supply current through controlling electrode 270 to control the potential of electrolyte medium 254, as monitored by reference electrode 218. (Operational amplifier 210 is maintained in the balanced state when feedback current through resistor 213 is equal and opposite to the current through resistor 216. Therefore, when a constant voltage is provided by voltage source 220, the output of operational amplifier 212 and also reference electrode 218 will be maintained at constant potential with respect to circuit ground.) The resultant current through semiconductor 250 is converted to a voltage signal by operational amplifier 222 configured with feedback resistor 224.

In certain cases it is desirable to monitor the DC component of the current passing through the silicon electrode under conditions where the silicon electrode is either dark or illuminated by a light source. In this configuration, the circuit is operated in the CP mode and the voltage output of opeational amplifier 222, which is, a current-to-voltage converter, is fed to a recorder. The voltage to the recorder is proportional to the DC component of the current through the silicon electrode.

The voltage at the outpoint of operational amplifier 222 is proportional to the current through semiconductor 250 and the constant of proportionality relating the voltage and the current is the resistance of resistor 224. Semiconductor region 255 is that region of semiconductor 250 which is substantially adjacent to electronically conducting layer 253. This is the so-called space-charge region of the Schottkey barrier formed between semiconductor 250 and electronically conducting layer 253. Semiconductor 250 may be biased electrically by voltage source 220, so as to cause depletion of charge carriers in semiconductor region 255.

For n-type semiconductors, this condition will occur when electrolyte 254 is negatively biased with respect to semiconductor 250. For p-type semiconductors, the opposite is true; depletion occurs when electrolyte 254 is positively biased with respect to semiconductor 250. After the depletion of charge carriers, no substantial current flows through semiconductor 250 because semiconductor region 255 is in the nonconducting state. Semiconductor region 255, however, becomes conductive when photogenerated charge carriers are caused to exist in the region upon illumination of semiconductor 250. Upon the illumination of a p-type semiconductor, current will flow through a circuit comprising: operational amplifier 210, controlling electrode 270, electrolyte 254, electronically conductive layer 253, semiconductor 250, and lead 276, when an electron acceptor (oxidant) species is present in electrolyte 254 at the surface of conductive layer 253. Reciprocally, upon the illumination of an n-type semiconductor, current will flow through the above circuit when an electron donor (reductant) species is present in electrolyte 254 at the surface of conducting layer 253. Thus, measurement of current or charge flowing through the circuit following the illumination provides a measure of the amount of oxidant or reductant species present in electrolyte 254 at the surface of conductive layer 253.

A multiplicity of separate conducting layers 253 may be present. Each conducting layer is similar to conducting layer 253 and each traverses a separate perforation in insulator 252. The separate conducting layers may be utilized to monitor the presence of redox substances at a multiplicity of separate sites in electrolyte medium 254. Alternatively, a device having such a multiplicity of separate conducting layers may be employed to monitor the presence of redox substances in a multiplicity of separate electrolyte media. If the media are separate, either a salt bridge (i.e., a common electrolyte connection) must be used to connect the separate media, or separate electrodes, such as reference electrode 218 and controlling electrode 220, must be employed separately in the separate electrolyte media.

In actual operation, regions of semiconductor 250 near the separate conducting layers 253 would be illuminated, one at a time, and the current for each region would be measured separately. A background measurement where none of the regions was illuminated would be subtracted from each of the measurements. Alternatively, each of the regions can be illuminated with light modulated at different frequencies. This will give rise to amplitude-modulated currents at the individual frequencies. The Faradaic current at each of the conductive layers may be related to the amplitude of the current at the perspective frequencies of light intensity modulation after first substracting the capacitive charging current. The semiconductor would be chosen to be either n-type or p-type depending upon whether a reductant or an oxidant, respectively, was being detected in the electrolyte medium.

An assay could be carried out as follows: A carbohydrate substance with lectin-binding moieties is either chemically linked or physically adsorbed onto the surface of conducting layer 253 which, in turn, is affixed to a p-type semiconductor substrate. Next a solution containing an enzyme, such as cholesterol esterase conjugated to lectin is introduced into container 256. After a sufficient time for adsorption of the conjugate to the surface of conducting layer 253, the compartment would be washed with an approximately buffered wash solution. Next added would be a sample solution buffered to pH 6.7 and containing the following: An unknown sample or a standard; antibody to an analyte, e.g., morphine; the analyte conjugated to a cholesterol esterase inhibitor; the enzyme cholesterol oxidase; the enzyme horseradish peroxidase; potassium ferrocyanide; and a cholesterol esterase substrate such as cholesterol acetate. Container 256 then would be filled with the sample and buffered solution, and any overflow withdrawn.

The hydrolysis of cholesterol ester by cholesterol esterase results in production of cholesterol, which is oxidized to produce $H_2O_2$, which oxidizes ferrocyanide to ferricyanide in a reaction catalyzed by the horseradish peroxidase. The ferricyanide produced results in a direct current upon irradation of the medium adjacent to the photoresponsive electrode. In this case, the electrode could be boron-doped silicon (i.e., a p-type semiconductor). The rate of production of ferricyanide would be inversely related to the amount of analyte in the sample, because analyte in the sample would bind to the anti-analyte antibody thereby preventing the antibody from binding to the analyte-enzyme inhibitor conjugate. Thus, more active anzyme inhibitor would be present causing the rate of ferricyanide production to be diminished.

After sufficient time for reaction to occur to obtain a detectable signal at the concentration range of interest, the photoresponsive electrode would be irradiated in the region under electrically conducting layer 253 and the resulting direct current detected by means of operational amplifier 222.

After removal of the assay medium and washing the container, a concentrated saccharide solution then would be introduced into the container, repetitively, until all of the enzyme had been removed from the surface. The container then would be washed with a wash solution to remove all of the unbound saccharide and then followed by introduction of the enzyme-lectin conjugate to restore the container to its original state for performing an essay.

As is evident from the above results, the subject invention provides for an accurate device which has a wide variety of applications. In accordance with the subject invention, an internal standard is provided which can be used to insure that changes in the circuitry can be corrected, so that errors due to changes in the reference electrode or other aspects of the device may be substracted from the observed result. The subject invention can be used for measuring directly media involving redox potentials or enzymes providing a change in redox potential. Alternatively, the subject invention can be used for measuring indirectly a wide variety of analytes by coupling an analyte into a system which allows for a change in redox potential of a medium in relation into the amount of analyte present. Of particular interest is the use of enzymes which produce an agent which can serve as a member of a redox couple or be coupled to another redox couple.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A field effect device for determining the redox potential of a liquid electrolyte medium, said device comprising:

as a detection unit:
   (i) a base photoresponsive semiconductive layer;
   (ii) an insulative layer covering at least a portion of a surface of said semiconductive layer; and
   (iii) an electronically conductive layer mounted on said insulative layer or mounted on said semiconductive layer at the uncovered portion of said surface;

light irradiation means for irradiating said base layer to produce minority carriers in juxtaposition to said electronically conductive layer; and means for connecting said base layer to a circuit.

2. A device according to claim 1, further comprising:
holding means for retaining a liquid electrolyte medium in contact with said electronically conductive layer.

3. A device according to claim 1, further comprising a plurality of said detection elements, each of said detection elements joined to said same connecting means.

4. A field effect device for determining the state of a medium in relation to a redox potential standard, said device comprising:
a detection element comprising a base semiconductor layer, an insulating layer covering at least a portion of a surface of said semiconductor layer, a metal layer mounted on said insulative layer or said base layer at the exposed portion of said surface, said metal layer having a medium contacting surface and said base layer having an irradiation receiving surface for forming minority carriers in juxtaposition to said medium contacting surface;
irradiation means for irradiating said irradiation receiving surface to produce a photoinduced signal;
means, connected to said detection element, for polarizing said detection element;
holding means for retaining one or more media in which determinations are to be made in contact with said medium contacting surface; and
a circuit for measuring the change in photoinduced electrical signal from said detection element as a result of the redox potential of a medium, wherein said circuit includes a high resistance element when said metal layer is in contact with said base layer.

5. A device according to claim 4, wherein said semiconductor layer is a plurality of individual doped silicon microchips.

6. A device according to claim 5, wherein said individual microchips are individually connected to said measuring means.

7. A device according to claim 4, wherein said irradiation means is programmed to provide regular light pulses.

8. A device according to claim 4, wherein said detection element comprises a single doped silicon chip.

9. A device according to claim 4, including a reference electrode connected to said circuit.

10. A field effect device for determining the state of an assay medium in relation to a pH, ion concentration or redox potential standard, said device comprising:
a detection element comprising a base semiconductor layer, an intermediate insulating layer covering at least a portion of said surface of said semiconductive layer, a metal layer mounted on and covering only a portion of said insulative layer, each of said metal layer and insulative layer having a medium contacting surface and said base layer having an irradiation receiving surface for forming minority carriers in juxtaposition to said medium contacting surface;
irradiation means for irradiating said irradiation receiving surface to provide a photoinduced signal;
means, connected to said detection element, for polarizing said element;
holding means for retaining one or media in which determinations are to be made in contact with said medium contacting surface; and
a circuit for measuring the change in a photoinduced electrical signal from said detection element as a result of a change in the redox potential, an ion concentration and/or pH of a medium.

11. A device according to claim 10, wherein at least one of said redox potential, ion concentration or pH is a constant system and at least one of the remaining is a variable system and said circuit further comprises means for comparing the photoinduced signal as a result of the constant system to the photoinduced electrical signal from the variable system to relate the difference beteen said photoinduced electrical signal from said constant system and said variable system to a pH, ion concentration or redox potential of the variable system.

12. A device according to claim 10, further comprising:
as a polarizing means, a counterelectrode connected to said circuit and positioned for contacting said medium.

13. A device according to claim 12, wherein said polarizing means further comprises means for applying a DC bias potential across said detection element and said counterelectrode.

14. A device according to claim 10, wherein said circuit comprises:
means for ramping the potential over a predetermined voltage range; and
said irradiating is programmed to provide regular light pulses to provide a photoinduced alternating current or alternating voltage.

15. A device according to claim 14, wherein said irradiation means irradiates said irradiation receiving surface in relation to said medium contacting surface with a single light source.

16. A device according to claim 14, wherein said circuit scans the change in alternating current or alternating voltage, with change in potential and relates the change in alternating current or alternating voltage in relation to at least two of the parameters consisting of pH, ion concentration, and redox potential of said medium, wherein one of said parameters is held constant and the other of said two parameters is of unknown value and allowed to vary.

17. A device according to claim 10, further comprising:
at least one member of a specific binding pair nondiffusively bound to a support in juxtaposition to said metal surface or said insulative layer.

18. A device according to claim 17, wherein said member is an immunoglobulin.

19. A field effect device for making a determination in relation to a variable system and adjusting said variable system determination in relation to a determination made in relation to a constant system, wherein one of said systems is a redox system and the other system is a pH or ion concentration system, said device employing a photoinduced signal as a result of irradiation of a photoresponsive element, said device comprising:
a detection element comprising a base semiconductor layer, an insulating layer covering at least a portion of a surface of said semiconductor layer, a metal layer mounted on and covering only a portion of said insulative layer or on said semiconductor layer surface at an uncovered portion, each of said metal layer and insulative layer having a medium contacting surface and said base layer having an irradiation receiving surface for forming minority carriers in juxtaposition to said metal layer and said insulative layer, wherein said metal layer is for obtaining a redox related signal and said insulative layer is for obtaining a pH or ion concentration related signal;

a counterelectrode;

irradiation means for irradiating said irradiation receiving surface to produce a photoinduced signal;

polarizing means, connected to said detection element, for polarizing said detection element;

holding means for retaining one or more media in which determinations are to be made in contact with said medium contacting surfaces;

a circuit connecting said detection element and counterelectrode for measuring the change in photoinduced electrical signal from said detection element as a result of the redox potential of a medium and as a result of the pH or an ion concentration of a medium, for determining a relationship between the signal from the variable system and the signal from said constant system.

20. A device according to claim 19, wherein said polarizing means comprises means for applying a DC bias potential across said detection element and said counterelectrode.

21. A device according to claim 19, wherein said circuit comprises:
means for ramping the potential over a predetermined voltage range; and
said irradiation means is programmed to provide regular light pulses to produce a photoinduced alternating current or alternating voltage.

22. A device according to claim 21, wherein said irradiation means irradiates said irradiation receiving with a single light source.

23. A device according to claim 21, wherein said circuit scans the change in alternating current or alternating voltage with change in potential and relates the change in alternating current or alternating voltage to a difference between the constant system and the variable system.

24. A device according to claim 19, further comprising:
at least one member of a specific binding pair nondiffusively bound to a support in juxtaposition to said metal surface or to said insulative layer.

25. A device according to claim 24, wherein said member is an immunoglobulin.

26. A method for measuring a state of a medium, wherein said state may be related directly or indirectly to redox potential, pH, or an ion concentration, wherein redox potential and one other state is measured, and one of said redox potential, pH, or ion concentration is a variable system of interest and the other is a constant system, said method employing a device comprising:
a detection element comprising a base semiconductor layer, an intermediate insulating layer covering at least a portion of a surface of said semiconductive layer, a metal layer mounted on and covering only a portion of said insulative layer, each of said metal layer and insulative layer having a medium contacting surface and said base layer having an irradiation receiving surface for forming minority carriers in juxtaposition to said medium contacting surfaces, wherein said metal layer is for obtaining a redox related signal and said insulative layer is for obtaining a pH or ion related signal;

an irradiation means for irradiating said irradiation receiving surface to produce a photoinduced signal;

a counterelectrode;

a circuit connecting said detection element and said counterelectrode;

a holding means for retaining a medium in electrical contact with said detection element and said counterelectrode;

said method comprising:
introducing said medium to provide electrical communication between said detection element and said counterelectrode;
irradiating said irradiation receiving surface to produce a photoinduced signal:
determining the photoinduced signal from the constant system as compared to the signal related to the variable system, and relating the difference in said signals to the state of said medium as to said variable system.

27. A method according to claim 26, wherein said circuit comprises:
means for ramping the potential over a predetermined voltage range, and said irradiation means is programmed to provide regular light pulses to produce a photoinduced alternating current or alternating voltage.

28. A method according to claim 26, wherein said irradiation receiving surface for forming minority carriers in juxtaposition with said metal layer contacting surface, and said irradiation receiving surface for forming minority carriers in juxtaposition with said insulative layer medium contacting surface are irradiated simultaneously from a common light source.

29. A method according to claim 26, wherein said redox potential, pH or ion concentration is modulated by an enzymatic reaction.

30. A method according to claim 29, wherein said enzymatic reaction is electrically coupled to said metal layer by means of a redox species in said medium.

31. A method according to claim 26, wherein said device includes a reference electrode to provide a standard signal from said constant system.

32. A method for measuring an analyte in a sample, said analyte capable of reacting directly or indirectly with a redox modulating system which comprises a redox couple, said measuring comprising measuring the change in the redox potential of a sample containing medium employing a device comprising:
a detection element comprising a base semiconductor layer, an intermediate insulating layer covering at least a portion of a surface of said semiconductive layer, a metal layer mounted on and covering only a portion of said insulative layer, each of said metal layer and insulative layer having a medium contacting surface and said base layer having an irradiation receiving surface for forming minority carriers in juxtaposition to said medium contacting surfaces, wherein said metal layer is for obtaining a redox related signal and said insulative layer is for obtaining a pH related signal or ion related signal; and a counterelectrode;

said method comprising:
introducing said medium to provide electrical communication between said detection element and said counterelectric and to provide an assay medium, wherein said assay medium comprises said sample, a redox modulating system capable of reacting directly or indirectly with said analyte, and sufficient buffer to maintain a constant pH or sufficient ion to maintain a constant ion concentration;

irradiating said irradiation receiving surface to produce a photoinduced signal;

determining said pH related or ion related photoinduced signal as compared to said redox related photoinduced signal and standardizing the difference between said pH or ion related photoinduced signal and said redox related photoinduced signal, wherein said difference is related to a known amount of analyte.

33. A method according to claim 32, wherein said redox modulating system comprises at least one oxidoreductase and an inorganic redox couple.

34. A method for measuring a glucose containing sample by means of measuring the change in the redox potential of a sample containing medium employing a device comprising:

a detection element comprising a base semiconductor layer, an intermediate insulating layer covering at least a portion of a surface of said semiconductive layer, a metal layer mounted on and covering only a portion of said insulative layer, each of said metal layer and insulative layer having a medium contacting surface and said base layer having an irradiation receiving surface for forming minority carriers in juxtaposition to said medium contacting surfaces, wherein said metal layer is for obtaining a redox related signal and said insulative layer is for obtaining a pH related signal or ion related signal;

said method comprising:

introducing said medium to provide electrical communication between said detection element and said counterelectrode and to provide an assay medium, wherein said assay medium comprises said sample, glucose oxidase, glucose, a redox system capable of reacting with hydrogen peroxide and communicating the redox potential to said metal layer, and sufficient buffer to maintain a substantially constant pH;

irradiating said irradiation receiving surface to produce a photoinduced signal;

determining said pH related signal as compared to said redox related signal and standardizing the rate of change in the difference between said pH related signal and said redox potential related signal to a known amount of glucose.

35. A method for measuring the amount of analyte in a sample by measuring the redox potential of a sample containing medium employing a device comprising:

detection element comprising a base semiconductor layer, an intermediate insulating layer covering at least a portion of a surface of said semiconductive layer, a metal layer mounted on and covering only a portion of said insulative layer, each of said metal layer and insulative layer having a medium contacting surface and said base layer having an irradiation receiving surface for forming minority carriers in juxtaposition to said medium contacting surfaces, wherein said metal layer is for obtaining a redox related signal and said insulative layer is for obtaining a pH or ion related signal; and a counterelectrode; and a member of a specific binding pair nondiffusively bound in juxtaposition to said metal layer or said insulative layer;

said method comprising:

introducing said medium to provide electrical communication between said detection element and said counterelectrode to provide an assay medium, wherein said assay medium comprises, a redox modulating system comprising an oxidoreductase-specific binding pair member conjugate, a redox couple, oxidoreductase substrate and any cofactors, and wherein the total oxidoreductase reaction rate in said medium is related to the amount of analyte in said sample;

irradiating said irradiation receiving surface to produce a photoinduced signal;

determining said pH or ion related signal as compared to said redox related signal and relating the difference between said pH or ion related signal and said redox related signal to the amount of analyte in said sample.

36. A method according to claim 35, further comprising:

combining said sample with said conjugate for sufficient time for reaction to form a complex containing mixture, wherein upon said introducing, said nondiffusively bound specific binding member is able to bind with said conjugate;

washing said support to remove any nonspecifically bound conjugate; and adding said redox couple, enzyme substrate and any cofactors to produce said assay medium.

37. A method according to claim 35, wherein said conjugate changes enzyme activity when bound to the complementary member of said analyte.

38. A method of measuring a state of a medium by an amperometric measurement, wherein said state may be related directly or indirectly to redox potential, pH, or an ion concentration, wherein redox potential and one other state is measured, and one of said redox potential, pH, or ion concentration is a variable system of interest and the other is a constant system, said method employing a device comprising:

a detection element comprising a base semiconductor layer, an intermediate insulating layer covering only a portion of a surface of said semiconductor layer, a electronically conductive layer mounted on said surface at an uncovered portion of said surface, each of said electronically conductive layer and insulative layer having a medium contacting surface and said base layer having an irradiation receiving surface for forming minority carriers in a region in juxtaposition to said medium contacting surfaces, said region being reverse biased, wherein said electronically conductive layer is for obtaining a Faradaic current and said insulative layer is for obtaining a pH or ion related signal;

a counterelectrode;

a circuit connecting said detection element and said counterelectrode;

a holding means for retaining a medium in electrical contact with said detection element and said counterelectrode;

said method comprising:

introducing said medium to provide electrical communication between said detection element and said counterelectrode;

irradiating said irradiation receiving surface to produce a photoinduced signal;

determining the photoinduced signal from the constant system and determining the resulting photoinduced amperometric signal related to the variable system, and relating said amperometric signal to the state of said medium.

* * * * *